(12) United States Patent
Hoey et al.

(10) Patent No.: US 9,198,708 B2
(45) Date of Patent: *Dec. 1, 2015

(54) SYSTEMS AND METHODS FOR PROSTATE TREATMENT

(71) Applicant: NxThera, Inc., Maple Grove, MN (US)

(72) Inventors: Michael Hoey, Shoreview, MN (US); Mark Schrom, Forest Lake, MN (US); Stephanos Paulos, Little Canada, MN (US); Randall Beyreis, Corcoran, MN (US)

(73) Assignee: NXTHERA, INC., Maple Grove, MN (US)

( * ) Notice: Subject to any disclaimer, the term of this patent is extended or adjusted under 35 U.S.C. 154(b) by 96 days.

This patent is subject to a terminal disclaimer.

(21) Appl. No.: 14/106,388

(22) Filed: Dec. 13, 2013

(65) Prior Publication Data

US 2014/0107637 A1    Apr. 17, 2014

Related U.S. Application Data

(63) Continuation of application No. 13/072,573, filed on Mar. 25, 2011, now Pat. No. 8,632,530.

(60) Provisional application No. 61/317,358, filed on Mar. 25, 2010.

(51) Int. Cl.
*A61B 18/04*    (2006.01)
*A61B 18/00*    (2006.01)

(52) U.S. Cl.
CPC ....... *A61B 18/04* (2013.01); *A61B 2018/00035* (2013.01); *A61B 2018/00547* (2013.01); *A61B 2018/00982* (2013.01); *A61B 2018/048* (2013.01)

(58) Field of Classification Search
CPC .......... A61B 18/04; A61B 2018/0035; A61B 2018/00547; A61B 2018/00982; A61B 2018/048
See application file for complete search history.

(56) References Cited

U.S. PATENT DOCUMENTS

| 408,899 A | 8/1889 | Small |
|---|---|---|
| 1,719,750 A | 7/1929 | Bridge et al. |

(Continued)

FOREIGN PATENT DOCUMENTS

| CN | 2061443 U | 9/1990 |
|---|---|---|
| CN | 2418844 Y | 2/2001 |

(Continued)

OTHER PUBLICATIONS

Hoey et al.; U.S. Appl. No. 14/453,254 entitled "Systems and Methods for Treatment of BPH," filed Aug. 6, 2014.

(Continued)

*Primary Examiner* — Michael Peffley
*Assistant Examiner* — Daniel Fowler
(74) *Attorney, Agent, or Firm* — Shay Glenn LLP

(57) ABSTRACT

A vapor delivery needle is provided that may include any of a number of features. One feature of the energy delivery probe is that it can apply condensable vapor energy to tissue, such as a prostrate, to shrink, damage, denaturate the prostate. In some embodiments, the needle can ablate a continuous lobe region in the prostate parallel to the urethral wall. Another feature of the vapor delivery needle is that it can introduce a cooling fluid into the urethra during treatment. Methods associated with use of the energy delivery probe are also covered.

20 Claims, 18 Drawing Sheets

(56) References Cited

U.S. PATENT DOCUMENTS

| | | |
|---|---|---|
| 4,672,963 A | 6/1987 | Barken |
| 4,920,982 A | 5/1990 | Goldstein |
| 4,950,267 A | 8/1990 | Ishihara et al. |
| 5,117,482 A | 5/1992 | Hauber |
| 5,222,185 A | 6/1993 | McCord, Jr. |
| 5,300,099 A | 4/1994 | Rudie |
| 5,312,399 A | 5/1994 | Hakky et al. |
| 5,330,518 A | 7/1994 | Neilson et al. |
| 5,366,490 A | 11/1994 | Edwards et al. |
| 5,370,609 A | 12/1994 | Drasler et al. |
| 5,370,675 A | 12/1994 | Edwards et al. |
| 5,370,677 A | 12/1994 | Rudie et al. |
| 5,385,544 A | 1/1995 | Edwards et al. |
| 5,409,453 A | 4/1995 | Lundquist et al. |
| 5,413,588 A | 5/1995 | Rudie et al. |
| 5,421,819 A | 6/1995 | Edwards et al. |
| 5,435,805 A | 7/1995 | Edwards et al. |
| 5,464,437 A | 11/1995 | Reid et al. |
| 5,470,308 A | 11/1995 | Edwards et al. |
| 5,470,309 A | 11/1995 | Edwards et al. |
| 5,484,400 A | 1/1996 | Edwards et al. |
| 5,499,998 A | 3/1996 | Meade |
| 5,531,676 A | 7/1996 | Edwards et al. |
| 5,542,915 A | 8/1996 | Edwards et al. |
| 5,542,916 A | 8/1996 | Hirsch et al. |
| 5,545,171 A | 8/1996 | Sharkey et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,673 A | 9/1996 | Edwards et al. |
| 5,588,960 A | 12/1996 | Edwards et al. |
| 5,591,125 A | 1/1997 | Edwards et al. |
| 5,599,294 A | 2/1997 | Edwards et al. |
| 5,601,591 A | 2/1997 | Edwards et al. |
| 5,628,770 A | 5/1997 | Thome et al. |
| 5,630,794 A | 5/1997 | Lax et al. |
| 5,645,528 A | 7/1997 | Thome |
| 5,667,488 A | 9/1997 | Lundquist et al. |
| 5,672,153 A | 9/1997 | Lax et al. |
| 5,709,680 A | 1/1998 | Yates et al. |
| 5,720,718 A | 2/1998 | Rosen et al. |
| 5,720,719 A | 2/1998 | Edwards et al. |
| 5,776,176 A | 7/1998 | Rudie |
| 5,792,070 A | 8/1998 | Kauphusman et al. |
| 5,797,903 A | 8/1998 | Swanson et al. |
| 5,800,486 A | 9/1998 | Thome et al. |
| 5,807,395 A | 9/1998 | Mulier et al. |
| 5,830,179 A | 11/1998 | Mikus et al. |
| 5,843,144 A | 12/1998 | Rudie et al. |
| 5,849,011 A | 12/1998 | Jones et al. |
| 5,861,021 A | 1/1999 | Thome et al. |
| 5,871,481 A | 2/1999 | Kannenberg et al. |
| 5,873,877 A | 2/1999 | McGaffigan et al. |
| 5,897,553 A | 4/1999 | Mulier et al. |
| 5,899,932 A | 5/1999 | Dann et al. |
| 5,938,692 A | 8/1999 | Rudie |
| 5,944,715 A | 8/1999 | Goble et al. |
| 5,957,922 A | 9/1999 | Imran |
| 5,964,752 A | 10/1999 | Stone |
| 5,964,756 A | 10/1999 | McGaffigan et al. |
| 5,976,123 A | 11/1999 | Baumgardner et al. |
| 5,987,360 A | 11/1999 | McGrath et al. |
| 5,990,465 A | 11/1999 | Nakaoka et al. |
| 6,007,571 A | 12/1999 | Neilson et al. |
| 6,009,351 A | 12/1999 | Flachman |
| 6,017,358 A | 1/2000 | Yoon et al. |
| 6,017,361 A | 1/2000 | Mikus et al. |
| 6,036,631 A | 3/2000 | McGrath et al. |
| 6,036,713 A | 3/2000 | Kieturakis |
| 6,053,909 A | 4/2000 | Shadduck |
| 6,063,081 A | 5/2000 | Mulier et al. |
| 6,067,475 A | 5/2000 | Graves et al. |
| 6,077,257 A | 6/2000 | Edwards et al. |
| 6,113,593 A | 9/2000 | Tu et al. |
| 6,122,551 A | 9/2000 | Rudie et al. |
| 6,123,083 A | 9/2000 | McGrath et al. |
| 6,147,336 A | 11/2000 | Oshijima et al. |
| 6,148,236 A | 11/2000 | Dann |
| 6,156,036 A | 12/2000 | Sussman et al. |
| 6,161,049 A | 12/2000 | Rudie et al. |
| 6,179,805 B1 | 1/2001 | Sussman et al. |
| 6,179,836 B1 | 1/2001 | Eggers et al. |
| 6,206,847 B1 | 3/2001 | Edwards et al. |
| 6,210,404 B1 | 4/2001 | Shadduck |
| 6,223,085 B1 | 4/2001 | Dann et al. |
| 6,231,591 B1 | 5/2001 | Desai |
| 6,238,389 B1 | 5/2001 | Paddock et al. |
| 6,238,391 B1 | 5/2001 | Olsen et al. |
| 6,238,393 B1 | 5/2001 | Mulier et al. |
| 6,241,702 B1 | 6/2001 | Lundquist et al. |
| 6,258,087 B1 | 7/2001 | Edwards et al. |
| 6,272,384 B1 | 8/2001 | Simon et al. |
| 6,287,297 B1 | 9/2001 | Woodruff et al. |
| 6,302,903 B1 | 10/2001 | Mulier et al. |
| 6,312,391 B1 | 11/2001 | Ramadhyani et al. |
| 6,315,777 B1 | 11/2001 | Comben |
| 6,348,039 B1 | 2/2002 | Flachman et al. |
| 6,398,759 B1 | 6/2002 | Sussman et al. |
| 6,409,722 B1 | 6/2002 | Hoey et al. |
| 6,423,027 B1 | 7/2002 | Gonon |
| 6,440,127 B2 | 8/2002 | McGovern et al. |
| 6,494,902 B2 | 12/2002 | Hoey et al. |
| 6,496,737 B2 | 12/2002 | Rudie et al. |
| 6,508,816 B2 | 1/2003 | Shadduck |
| 6,517,534 B1 | 2/2003 | McGovern et al. |
| 6,524,270 B1 | 2/2003 | Bolmsjo et al. |
| 6,537,248 B2 | 3/2003 | Mulier et al. |
| 6,537,272 B2 | 3/2003 | Christopherson et al. |
| 6,544,211 B1 | 4/2003 | Andrew et al. |
| 6,551,300 B1 | 4/2003 | McGaffigan |
| 6,565,561 B1 | 5/2003 | Goble et al. |
| 6,575,929 B2 | 6/2003 | Sussman et al. |
| 6,575,968 B1 | 6/2003 | Eggers et al. |
| 6,579,270 B2 | 6/2003 | Sussman et al. |
| 6,589,201 B1 | 7/2003 | Sussman et al. |
| 6,607,529 B1 | 8/2003 | Jones et al. |
| 6,638,275 B1 | 10/2003 | McGaffigan et al. |
| 6,640,139 B1 | 10/2003 | Ueberle |
| 6,669,694 B2 | 12/2003 | Shadduck |
| 6,676,628 B2 | 1/2004 | Sussman et al. |
| 6,706,039 B2 | 3/2004 | Mulier et al. |
| 6,716,252 B2 | 4/2004 | Lazarovitz et al. |
| 6,719,738 B2 | 4/2004 | Mehier |
| 6,726,696 B1 | 4/2004 | Houser et al. |
| 6,730,079 B2 | 5/2004 | Lovewell |
| 6,736,810 B2 | 5/2004 | Hoey et al. |
| 6,740,108 B1 | 5/2004 | Just et al. |
| 6,760,616 B2 | 7/2004 | Hoey et al. |
| 6,780,178 B2 | 8/2004 | Palanker et al. |
| 6,827,718 B2 | 12/2004 | Hutchins et al. |
| 6,855,141 B2 | 2/2005 | Lovewell |
| 6,887,237 B2 | 5/2005 | McGaffigan |
| 6,905,475 B2 | 6/2005 | Hauschild et al. |
| 6,911,028 B2 | 6/2005 | Shadduck |
| 6,969,376 B2 | 11/2005 | Takagi et al. |
| 6,974,455 B2 | 12/2005 | Garabedian et al. |
| 7,014,652 B2 | 3/2006 | Cioanta et al. |
| 7,041,121 B1 | 5/2006 | Williams et al. |
| 7,066,935 B2 | 6/2006 | Swoyer et al. |
| 7,089,064 B2 | 8/2006 | Manker et al. |
| 7,130,697 B2 | 10/2006 | Chornenky et al. |
| 7,238,182 B2 | 7/2007 | Swoyer et al. |
| 7,247,155 B2 | 7/2007 | Hoey et al. |
| 7,261,709 B2 | 8/2007 | Swoyer et al. |
| 7,261,710 B2 | 8/2007 | Elmouelhi et al. |
| 7,322,974 B2 | 1/2008 | Swoyer et al. |
| 7,328,068 B2 | 2/2008 | Spinelli et al. |
| 7,328,069 B2 | 2/2008 | Gerber |
| 7,335,197 B2 | 2/2008 | Sage et al. |
| 7,340,300 B2 | 3/2008 | Christopherson et al. |
| 7,369,894 B2 | 5/2008 | Gerber |
| 7,429,262 B2 | 9/2008 | Woloszko et al. |
| 7,437,194 B2 | 10/2008 | Skwarek et al. |
| 7,470,228 B2 | 12/2008 | Connors et al. |

(56) References Cited

U.S. PATENT DOCUMENTS

| | | |
|---|---|---|
| 7,549,987 B2 | 6/2009 | Shadduck |
| 7,865,250 B2 | 1/2011 | Mrva et al. |
| 7,894,913 B2 | 2/2011 | Boggs et al. |
| 7,959,577 B2 | 6/2011 | Schmitz et al. |
| 8,048,069 B2 | 11/2011 | Skwarek et al. |
| 8,216,217 B2 | 7/2012 | Sharkey et al. |
| 8,244,327 B2 | 8/2012 | Fichtinger et al. |
| 8,251,985 B2 | 8/2012 | Hoey et al. |
| 8,272,383 B2 | 9/2012 | Hoey et al. |
| 8,273,079 B2 | 9/2012 | Hoey et al. |
| 8,301,264 B2 | 10/2012 | Achenbach et al. |
| 8,313,485 B2 | 11/2012 | Shadduck |
| 8,372,065 B2 | 2/2013 | Hoey et al. |
| 8,388,611 B2 | 3/2013 | Shadduck et al. |
| 8,409,109 B2 | 4/2013 | Tiesma et al. |
| 8,419,723 B2 | 4/2013 | Shadduck et al. |
| 8,550,743 B2 | 10/2013 | Bonde et al. |
| 8,585,692 B2 | 11/2013 | Shadduck et al. |
| 8,632,530 B2 | 1/2014 | Hoey et al. |
| 8,900,223 B2 | 12/2014 | Shadduck |
| 2002/0078956 A1 | 6/2002 | Sharpe et al. |
| 2002/0177846 A1 | 11/2002 | Mulier et al. |
| 2003/0069575 A1 | 4/2003 | Chin et al. |
| 2003/0097126 A1 | 5/2003 | Woloszko et al. |
| 2003/0130575 A1 | 7/2003 | Desai |
| 2003/0206730 A1 | 11/2003 | Golan |
| 2004/0068306 A1 | 4/2004 | Shadduck |
| 2004/0186422 A1 | 9/2004 | Rioux et al. |
| 2004/0230316 A1 | 11/2004 | Cioanta et al. |
| 2005/0096629 A1 | 5/2005 | Gerber et al. |
| 2005/0124915 A1 | 6/2005 | Eggers et al. |
| 2005/0149020 A1 | 7/2005 | Jahng |
| 2005/0159676 A1 | 7/2005 | Taylor et al. |
| 2006/0135955 A1 | 6/2006 | Shadduck |
| 2006/0178670 A1 | 8/2006 | Woloszko et al. |
| 2006/0224154 A1 | 10/2006 | Shadduck et al. |
| 2006/0224169 A1 | 10/2006 | Weisenburgh, II et al. |
| 2006/0253069 A1 | 11/2006 | Li et al. |
| 2006/0276871 A1 | 12/2006 | Lamson et al. |
| 2007/0032785 A1 | 2/2007 | Diederich et al. |
| 2007/0038089 A1 | 2/2007 | Hatano et al. |
| 2007/0142846 A1 | 6/2007 | Catanese, III et al. |
| 2007/0179491 A1 | 8/2007 | Kratoska et al. |
| 2007/0197864 A1 | 8/2007 | Dejima et al. |
| 2008/0021484 A1 | 1/2008 | Catanese, III et al. |
| 2008/0021485 A1 | 1/2008 | Catanese, III et al. |
| 2008/0033232 A1 | 2/2008 | Catanese, III et al. |
| 2008/0033458 A1 | 2/2008 | McLean et al. |
| 2008/0033488 A1 | 2/2008 | Catanese, III et al. |
| 2008/0039833 A1 | 2/2008 | Catanese, III et al. |
| 2008/0039872 A1 | 2/2008 | Catanese, III et al. |
| 2008/0039874 A1 | 2/2008 | Catanese, III et al. |
| 2008/0039875 A1 | 2/2008 | Catanese, III et al. |
| 2008/0039876 A1 | 2/2008 | Catanese, III et al. |
| 2008/0039893 A1 | 2/2008 | McLean et al. |
| 2008/0039894 A1 | 2/2008 | Catanese, III et al. |
| 2008/0046045 A1 | 2/2008 | Yon et al. |
| 2008/0110457 A1 | 5/2008 | Barry et al. |
| 2008/0132826 A1 | 6/2008 | Shadduck et al. |
| 2008/0188811 A1 | 8/2008 | Kim |
| 2008/0208187 A1 | 8/2008 | Bhushan et al. |
| 2008/0249399 A1 | 10/2008 | Appling et al. |
| 2008/0262491 A1 | 10/2008 | Swoyer et al. |
| 2008/0269737 A1 | 10/2008 | Elmouelhi et al. |
| 2008/0269862 A1 | 10/2008 | Elmouelhi et al. |
| 2008/0275440 A1 | 11/2008 | Kratoska et al. |
| 2008/0297287 A1 | 12/2008 | Shachar et al. |
| 2008/0312497 A1 | 12/2008 | Elmouelhi et al. |
| 2009/0018553 A1 | 1/2009 | McLean et al. |
| 2009/0054871 A1 | 2/2009 | Sharkey et al. |
| 2009/0138001 A1 | 5/2009 | Barry et al. |
| 2009/0149846 A1 | 6/2009 | Hoey et al. |
| 2009/0199855 A1 | 8/2009 | Davenport |
| 2009/0216220 A1 | 8/2009 | Hoey et al. |
| 2009/0227998 A1 | 9/2009 | Aljuri et al. |
| 2009/0306640 A1 | 12/2009 | Glaze et al. |
| 2010/0016757 A1 | 1/2010 | Greenburg et al. |
| 2010/0049031 A1 | 2/2010 | Fruland et al. |
| 2010/0094270 A1 | 4/2010 | Sharma |
| 2010/0114083 A1 | 5/2010 | Sharma |
| 2010/0179416 A1 | 7/2010 | Hoey et al. |
| 2010/0193568 A1 | 8/2010 | Scheib et al. |
| 2010/0204688 A1 | 8/2010 | Hoey et al. |
| 2010/0256636 A1 | 10/2010 | Fernandez et al. |
| 2010/0262133 A1 | 10/2010 | Hoey et al. |
| 2010/0262137 A1 | 10/2010 | Nye et al. |
| 2010/0286679 A1 | 11/2010 | Hoey et al. |
| 2010/0292767 A1 | 11/2010 | Hoey et al. |
| 2010/0298948 A1 | 11/2010 | Hoey et al. |
| 2011/0060328 A1 | 3/2011 | Skwarek et al. |
| 2011/0077628 A1 | 3/2011 | Hoey et al. |
| 2011/0160648 A1 | 6/2011 | Hoey |
| 2011/0319759 A1 | 12/2011 | Liu et al. |
| 2012/0259271 A1 | 10/2012 | Shadduck et al. |
| 2012/0323167 A1 | 12/2012 | Hoey et al. |
| 2013/0006231 A1 | 1/2013 | Sharma et al. |
| 2013/0074847 A1 | 3/2013 | Hoey et al. |
| 2013/0158534 A1 | 6/2013 | Hoey et al. |
| 2013/0172867 A1 | 7/2013 | Shadduck et al. |
| 2014/0200568 A1 | 7/2014 | Sharma |
| 2015/0157384 A1 | 6/2015 | Hoey et al. |

FOREIGN PATENT DOCUMENTS

| | | |
|---|---|---|
| CN | 101072544 | 11/2007 |
| CN | 101257855 | 9/2008 |
| CN | 101006939 A | 11/2008 |
| CN | 101491458 A | 7/2009 |
| JP | 8-504613 A | 5/1996 |
| JP | 200014663 A | 1/2000 |
| JP | 2001-500763 A | 1/2001 |
| WO | WO 92/10142 A1 | 6/1992 |
| WO | WO 01/24715 A1 | 4/2001 |
| WO | WO 03/088851 A1 | 10/2003 |
| WO | WO 2006/004482 A1 | 1/2006 |
| WO | WO 2008/083407 A1 | 7/2008 |

OTHER PUBLICATIONS

Hoey et al.; U.S. Appl. No. 14/384,774 entitled "Induction coil vapor generator," filed Sep. 12, 2014.

Hai; Photoselective Vaporization Prostatectomy: A Palliative Treatment Option for Men with Urinary Obstruction Secondary to Prostate Cancer; PCRI Prost.Cancer Rsrch.Inst. Reprint.from PCRI Insights Nov. 2005, vol. 8(4); Dwnld from http://www.prostate-cancer.org/pcricms/node/233 on May 10, 2012; 4 pages.

Hoey et al.; U.S. Appl. No. 14/241,977 entitled "Systems and Methods for Prostate Treatment," filed Feb. 28, 2014.

US 5,326,343, 07/1994, Rudie et al. (withdrawn)

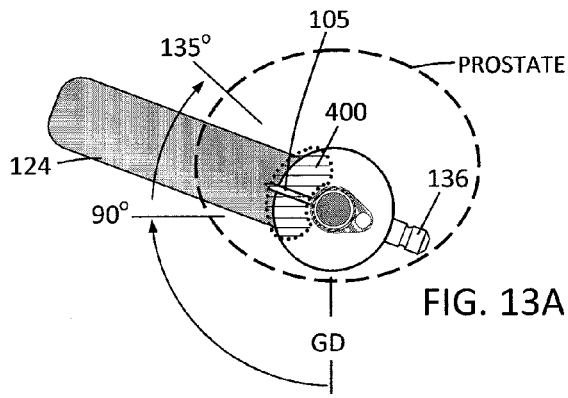
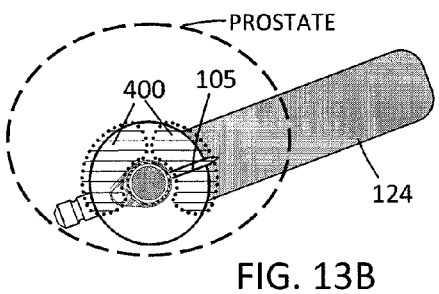
FIG. 13A  FIG. 13B
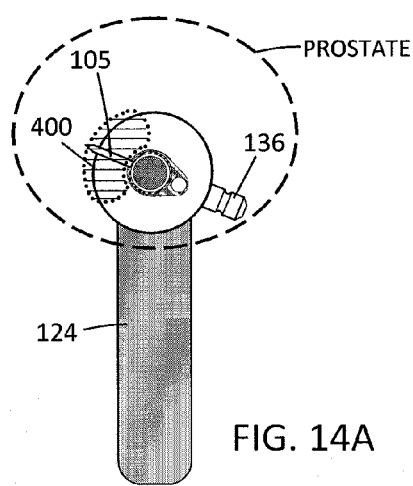
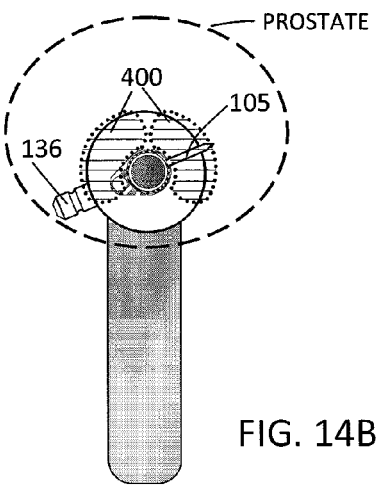
FIG. 14A  FIG. 14B
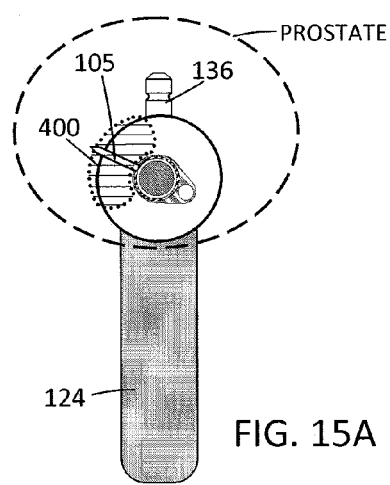
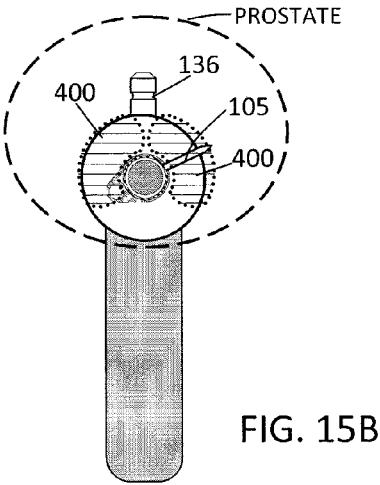
FIG. 15A  FIG. 15B

ADVANCING PROBE TRANS-URETHRALLY TO THE PATIENT'S PROSTATE

EXTENDING ENERGY APPLICATOR MEMBERS NO GREATER THAT 2 CM INTO A PLURALITY OF LOCATIONS IN PROSTATE LOBE

APPLYING ENERGY TO CREATE ABLATION ZONE PARALLEL ALONG A PORTION OF THE URETHRA

ADVANCING PROBE TRANS-URETHRALLY TO THE PATIENT'S PROSTATE

EXTENDING ENERGY APPLICATOR MEMBERS INTO A PLURALITY OF LOCATIONS IN PROSTATE LOBE

APPLYING ENERGY AT EACH LOCATION FOR A SELECTED INTERVAL AND IRRIGATING THE URETHRA WITH A COOLING FLUID THROUGHOUT THE ENERGY APPLICATION INTERVAL

SYSTEMS AND METHODS FOR PROSTATE TREATMENT

CROSS REFERENCE TO RELATED APPLICATIONS

This application is a continuation of U.S. patent application Ser. No. 13/072,573, filed Mar. 25, 2011, now U.S. Pat. No. 8,632,530, which application claims the benefit under 35 U.S.C. 119 of U.S. Provisional Patent Application No. 61/317,358, filed Mar. 25, 2010, titled "Systems and Methods for Prostate Treatment", both of which are incorporated by reference herein.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD OF THE INVENTION

The present invention relates to devices and related methods for treatment of benign prostatic hyperplasia using a minimally invasive approach.

BACKGROUND OF THE INVENTION

Benign prostatic hyperplasia (BPH) is a common disorder in middle-aged and older men, with prevalence increasing with age. At age 70, more than one-half of men have symptomatic BPH, and nearly 90% of men have microscopic evidence of an enlarged prostate. The severity of symptoms also increase with age with 27% of patients in the 60-70 age bracket having moderate-to-severe symptoms, and 37% of patients in their 70's suffering from moderate-to-severe symptoms.

The prostate early in life is the size and shape of a walnut and weighs about 20 grams. Prostate enlargement appears to be a normal process. With age, the prostate gradually increases in size to twice or more its normal size. The fibromuscular tissue of the outer prostatic capsule restricts expansion after the gland reaches a certain size. Because of such restriction on expansion, the intracapsular tissue will compress against and constrict the prostatic urethra thus causing resistance to urine flow.

FIG. 1 is a sectional schematic view the male urogenital anatomy, with the walnut-sized prostate gland 100 located below the bladder 105 and bladder neck indicated at 106. The walls 108 of bladder 105 can expand and contract to cause urine flow through the urethra 110, which extends from the bladder 105, through the prostate 100 and penis 112. The portion of urethra 110 that is surrounded by the prostate gland 100 is referred to as the prostatic urethra 120. The prostate 100 also surrounds the ejaculatory ducts 122 which have an open termination in the prostatic urethra 120. During sexual arousal, sperm is transported from the testes 124 by the ductus deferens 126 to the prostate 100 which provides fluids that combine with sperm to form semen during ejaculation. On each side of the prostate, the ductus deferens 126 and seminal vesicles 128 join to form a single tube called an ejaculatory duct 122. Thus, each ejaculatory duct 122 carries the seminal vesicle secretions and sperm into the prostatic urethra 120.

Referring to FIGS. 2A-2C, the prostate glandular structure can be classified into three zones: the peripheral zone, transition zone, and central zone. The peripheral zone PZ, which is the region forming the postero-inferior aspect of the gland, contains 70% of the prostate glandular elements in a normal prostate (FIGS. 2A-2C). A majority of prostate cancers (up to 80%) arise in the peripheral zone PZ. The central zone CZ surrounds the ejaculatory ducts 122 and contains about 20-25% of the prostate volume. The central zone is often the site of inflammatory processes. The transition zone TZ is the site in which benign prostatic hyperplasia develops, and contains about 5-10% of the volume of glandular elements in a normal prostate (FIG. 2C), but can constitute up to 80% of such volume in cases of BPH. The transition zone TZ consists of two lateral prostate lobes and the periurethral gland region indicated at 130. As can be understood from FIGS. 2A-2C, there are natural barriers around the transition zone TZ, i.e., the prostatic urethra 120, the anterior fibromuscular stroma FS, and a fibrous plane FP between the transition zone TZ and peripheral zone PZ. In FIGS. 2A-2C, the anterior fibromuscular stroma FS or fibromuscular zone can be seen and is predominantly fibromuscular tissue.

BPH is typically diagnosed when the patient seeks medical treatment complaining of bothersome urinary difficulties. The predominant symptoms of BPH are an increase in frequency and urgency of urination. BPH can also cause urinary retention in the bladder which in turn can lead to lower urinary tract infection (LUTI). In many cases, the LUTI then can ascend into the kidneys and cause chronic pyelonephritis, and can eventually lead to renal insufficiency. BPH also may lead to sexual dysfunction related to sleep disturbance or psychological anxiety caused by severe urinary difficulties. Thus, BPH can significantly alter the quality of life with aging of the male population.

BPH is the result of an imbalance between the continuous production and natural death (apoptosis) of the glandular cells of the prostate. The overproduction of such cells leads to increased prostate size, most significantly in the transitional zone which traverses the prostatic urethra.

In early stage cases of BPH, treatments can alleviate the symptoms. For example, alpha-blockers treat BPH by relaxing smooth muscle tissue found in the prostate and the bladder neck, which may allow urine to flow out of the bladder more easily. Such drugs can prove effective until the glandular elements cause overwhelming cell growth in the prostate.

More advanced stages of BPH, however, can only be treated by surgical interventions. A number of methods have been developed using electrosurgical or mechanical extraction of tissue, and thermal ablation or cryoablation of intracapsular prostatic tissue. In many cases, such interventions provide only transient relief, and there often is significant peri-operative discomfort and morbidity.

In a prior art thermal ablation method, RF energy is delivered to prostate tissue as schematically depicted in FIGS. 3A-3B. FIG. 3A depicts the elongated prior art RF needle being penetrated into a plurality of locations in a prostate lobe. In a first aspect of the prior art method, the elongated RF needle typically is about 20 mm in length, together with an insulator that penetrates into the lobe. The resulting RF treatment thus ablates tissue away from the prostatic urethra 120 and does not target tissue close to, and parallel to, the prostatic urethra 120. In another aspect of the prior art RF method, the application of RF energy typically extends for 1 to 3 minutes or longer which allows thermal diffusion of the ablation to reach the capsule periphery. Such prior art RF energy delivery methods may not create a durable effect, since smooth muscle tissue and alpha adrenergic receptors are not uniformly ablated around the prostatic urethra. As a result, tissue in the lobes can continue to grow and impinge on the urethra thus limiting long term effectiveness of the treatment.

SUMMARY OF THE INVENTION

In some embodiments, a method for treating benign prostatic hyperplasia of a prostate of a patient is provided, comprising inserting a vapor delivery needle through a urethral wall of the patient in a plurality of locations into a prostate lobe, delivering condensable water vapor through the needle into the prostate at each location, and ablating a continuous lobe region parallel to the urethral wall.

In some embodiments, the continuous lobe region is between a bladder neck and a verumontanum of the patient.

In some embodiments, the inserting step comprises inserting a tip of the vapor delivery needle 15 mm or less through the urethral wall into the prostate lobe.

In other embodiments, the ablating step comprises ablating the continuous lobe region extending less than 2 cm away from the urethral wall.

In some embodiments, the delivering step comprises delivering the condensable water vapor for less than 30 seconds.

In one embodiment, the method can further comprise introducing a cooling fluid into the urethra during the delivering step. Some embodiments further comprise inserting a vapor delivery tool shaft into the urethra, the vapor delivery needle being at least partially disposed within the shaft, the cooling fluid being introduced into the urethra through the shaft. Another embodiment is provided, further comprising introducing the cooling fluid into the urethra during the entire time condensable water vapor is delivered into the prostate.

Some embodiments can further comprise sensing a temperature within the urethra and controlling delivery of the condensable vapor based on the sensed temperature. In one embodiment, the sensing a temperature step comprises sensing a temperature of the vapor delivery needle.

In some embodiments, the method further comprises viewing the inserting step through an endoscope. In other embodiments, the method further comprises inserting a vapor delivery tool shaft into the urethra, the vapor delivery needle and the endoscope being at least partially disposed within the shaft. The method can further comprise introducing a cooling fluid into the urethra during the delivering step, the cooling fluid being introduced into the urethra through the shaft around the endoscope. In some embodiments, the method further comprises viewing with the endoscope a mark on the vapor delivery needle that is visible only when the needle is in one of a retracted position or a deployed position.

In some embodiments, the plurality of locations in the prostate lobe comprise a first plurality of locations longitudinally spaced along the urethra, the method further comprising inserting the vapor delivery needle through the urethral wall in a second plurality of locations in the prostate, the second plurality of locations being radially displaced from the first plurality of locations.

Another method for treating benign prostatic hyperplasia of a prostate of a patient is provided, comprising ablating a region of the prostate less than 2 cm away from urethra without ablating a peripheral lobe portion of the prostate.

In some embodiments, the method further comprises inserting an energy-emitting section of a needle into the prostate, wherein the ablating step comprises delivering energy to the prostate via the needle.

In some embodiments, the inserting step comprises inserting the needle transurethrally.

In other embodiments, the inserting step comprises inserting the needle transurethrally into the prostate in a plurality of locations, the region of the prostate comprising a continuous lobe region parallel to the urethral wall.

In an additional embodiment, the inserting step comprises inserting the needle transrectally.

A method for treating benign prostatic hyperplasia (BPH) is provided comprising positioning an energy-emitting section of needle in a plurality of locations in a prostate lobe adjacent the prostatic urethra, and delivering energy at each location for less than 30 seconds to thereby confine thermal ablation to lobe tissue adjacent the prostatic urethra and preventing thermal diffusion to peripheral lobe tissue.

In some embodiments, energy is delivered from a condensable vapor media.

In other embodiments, energy is delivered from a needle member introduced through a transurethral access path.

In some embodiments, the method further comprises introducing a cooling fluid into the urethra during the application of energy.

A method for treating benign prostatic hyperplasia of a prostate of a patient is provided, comprising inserting a vapor delivery needle through a urethral wall of the patient into the prostate, viewing the inserting step via an endoscope disposed in the urethra, delivering condensable water vapor through the needle into the prostate, and ablating prostate tissue within the prostate.

In some embodiments, the method further comprises inserting a vapor delivery tool shaft into the urethra, the needle and the endoscope both being at least partially disposed within the shaft.

Additionally, the method can further comprise, after the ablating step, retracting the needle, rotating the shaft and the needle within the urethra, inserting the vapor delivery needle through the urethral wall into a different location in the prostate, delivering condensable water vapor through the needle into the prostate, and ablating prostate tissue within the prostate.

In some embodiments, the method comprises supporting the shaft with a handle, the rotating step comprising rotating the handle with the shaft. In other embodiments, the method comprises supporting the shaft with a handle, the rotating step comprising rotating the shaft without rotating the handle. In some embodiments, the rotating step further comprises rotating the shaft and the needle without rotating the endoscope.

In one embodiment, the viewing step further comprises viewing a mark on the needle that is visible only when the needle is in one of a retracted position or a deployed position.

A vapor therapy system is provided, comprising a shaft adapted to be inserted into a male urethra, a vapor delivery needle in the shaft, the needle comprising a vapor exit port, a scope bore in the shaft sized to accommodate an endoscope, the bore having an opening oriented to permit a user to view a distal end of the vapor delivery needle through the endoscope, a water vapor source, and a vapor delivery actuator adapted to deliver water vapor from the water vapor source into the vapor delivery needle and out of the vapor exit port.

In some embodiments, the needle is movable between a retracted position in which a distal needle tip is within the shaft and a deployed position in which the distal needle tip extends from the shaft.

One embodiment of the system further comprises a vapor needle deployment mechanism adapted to move a tip of the needle transverse to the shaft. In some embodiments, the deployment mechanism is adapted to move the needle tip no more than 15 mm from the shaft.

In some embodiments, the system further comprises a marking on a distal tip portion of the vapor delivery needle. In one embodiment, the marking is visible through the bore when the needle is in the deployed position but not visible through bore opening when needle is in the retracted position.

Some embodiments of the system further comprise a needle-retraction actuator adapted to retract the needle into the shaft.

In some embodiments, the needle is configured to deliver water vapor over a predetermined length less that 15 mm from shaft. In other embodiments, the needle comprises a non-energy applicator portion that does not include a vapor exit port. In some embodiments, the non-energy applicator portion is approximately the thickness of the male urethra.

In some embodiments, the needle is a flexible polymer tube with sharp tip.

In other embodiments, the needle is insulated. In one embodiment, the insulated needle comprises a central bore surrounded by insulative air gap and an outer sleeve.

In some embodiments, the system further comprises an irrigation liquid source and an irrigation passage in the shaft extending from the irrigation liquid source to an irrigation liquid outlet. In one embodiment, the irrigation passage is within the bore. In another embodiment, the system comprises an irrigation actuator configured to irrigate a cooling fluid from the irrigation liquid source through the irrigation liquid outlet. In one embodiment, the irrigation liquid source is connected to the irrigation passage. In another embodiment, the irrigation actuator is configured to irrigate the cooling fluid when the vapor delivery actuator delivers water vapor.

In some embodiments, the system further comprises an interlock to prevent water vapor delivery without irrigation of the cooling fluid.

In some embodiments, the system further comprises a bridge element in the opening of the bore configured to prevent tissue from falling into the opening of the bore.

In some embodiments, the shaft has blunt distal tip and the opening of the bore is proximal to a distal end of the shaft.

In some embodiments, the system further comprises a handle connected to the shaft through an adjustably rotatable connector such that shaft can be rotated with respect to the handle. In some embodiments, the rotatable connector comprises rotational stops at preset angles.

In some embodiments, the system further comprises a temperature sensor operably connected to a controller to control vapor delivery based on a sensed temperature. In one embodiment, the temperature sensor is configured to sense needle temperature. In another embodiment, the temperature sensor is configured to sense shaft temperature.

A vapor therapy system is provided, comprising a shaft adapted to be inserted into a male urethra, a vapor delivery needle in the shaft, the needle comprising a vapor exit port, a vapor needle deployment mechanism adapted to move a tip of the needle transverse to the shaft no more than 15 mm from the shaft, a water vapor source; and a vapor delivery actuator adapted to deliver water vapor from the water vapor source into the vapor delivery needle and out of the vapor exit port.

In some embodiments, the vapor needle deployment mechanism comprises an actuator adapted to deploy an actuation force on the needle to deploy the needle.

In other embodiments, the vapor needle deployment mechanism further comprises a needle deployment spring.

In some embodiments, the system further comprises a vapor delivery interlock adapted to prevent delivery of water vapor from the vapor delivery needle unless the needle is deployed.

In some embodiments, the needle deployment mechanism further comprises a limit stop adapted to limit a deployment distance of the needle.

In some embodiments, the system further comprises a needle-retraction actuator adapted to retract the needle into the shaft.

In some embodiments, the system further comprises a scope bore in the shaft sized to accommodate an endoscope, the bore having an opening oriented to permit a user to view a distal end of the vapor delivery needle through the endoscope.

In other embodiments, the system further comprises a marking on a distal tip portion of the vapor delivery needle. In one embodiment, the marking is visible through the bore opening when the needle is in a deployment position but the marking is not visible through the bore opening when the needle is in a retracted position.

In some embodiments, the needle is a flexible polymer tube with a sharp tip.

In other embodiments, the needle is insulated. In some embodiments, the insulated needle comprises a central bore surrounded by an insulative air gap and an outer sleeve.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

FIGS. 13A-13B are schematic views of the probe of FIG. 4 in a head-on view in a prostate indicating the radial angle of the probe as it is rotated in situ to treat lateral prostate lobes.

FIGS. 14A-14B are schematic views similar to that of FIGS. 13A-13B showing a method of rotating certain components of the probe again indicating the radial angles of the penetrating microcatheter of the probe of FIG. 4, while leaving the probe handle in a non-rotated position.

FIGS. 15A-15B are schematic views similar to that of FIGS. 13A-13B showing a method of rotating other components of the probe, again indicating the radial angles of the penetrating microcatheter in the lateral lobes of the prostate while leaving the probe handle in a non-rotated position.

DETAILED DESCRIPTION OF THE INVENTION

In general, one method of the invention for treating BPH comprises introducing a heated vapor interstitially into the interior of a prostate, wherein the vapor controllably ablates prostate tissue. This method can utilize vapor for applied energy of between 50 calories and 200 calories per lobe in an office-based procedure. The method can cause localized ablation of prostate tissue, and more particularly the applied energy from vapor can be localized to ablate tissue adjacent the urethra without damaging prostate tissue that is not adjacent the urethra.

The present invention is directed to the treatment of BPH, and more particularly for ablating transitional zone prostate tissue without ablating peripheral zone prostate tissue.

In one embodiment, the present invention is directed to treating a prostate using convective heating in a region adjacent the prostatic urethra.

In one embodiment, the method of ablative treatment is configured to target smooth muscle tissue, alpha adrenergic receptors, and sympathetic nerve structures parallel to the prostatic urethra between the bladder neck region and the verumontanum region to a depth of less than 2 cm.

In one embodiment, the system includes a vapor delivery mechanism that delivers water vapor. The system can utilize a vapor source configured to provide vapor having a temperature of at least 60° C., 80° C., 100° C., 120° C., or 140° C.

In another embodiment, the system further comprises a computer controller configured to deliver vapor for an interval ranging from 1 second to 30 seconds.

In another embodiment, the system further comprises a source of a pharmacologic agent or other chemical agent or compound for delivery with the vapor. The agent can be an anesthetic, and antibiotic or a toxin such as Botox®. The agent can also be a sealant, an adhesive, a glue, a superglue or the like.

Another method of the invention provides a treatment for BPH that can use transrectal approach using a TRUS (ultrasound system as an imaging means to image the prostate, and navigate a vapor delivery tool to the treatment sites.

In another method of the invention, the tool or needle working end can be advanced manually or at least in part by a spring mechanism.

In another aspect of the invention, the system may contemporaneously deliver cooling fluids to the urethra during an ablation treatment to protect the interior lining of the urethra.

Figure 4:
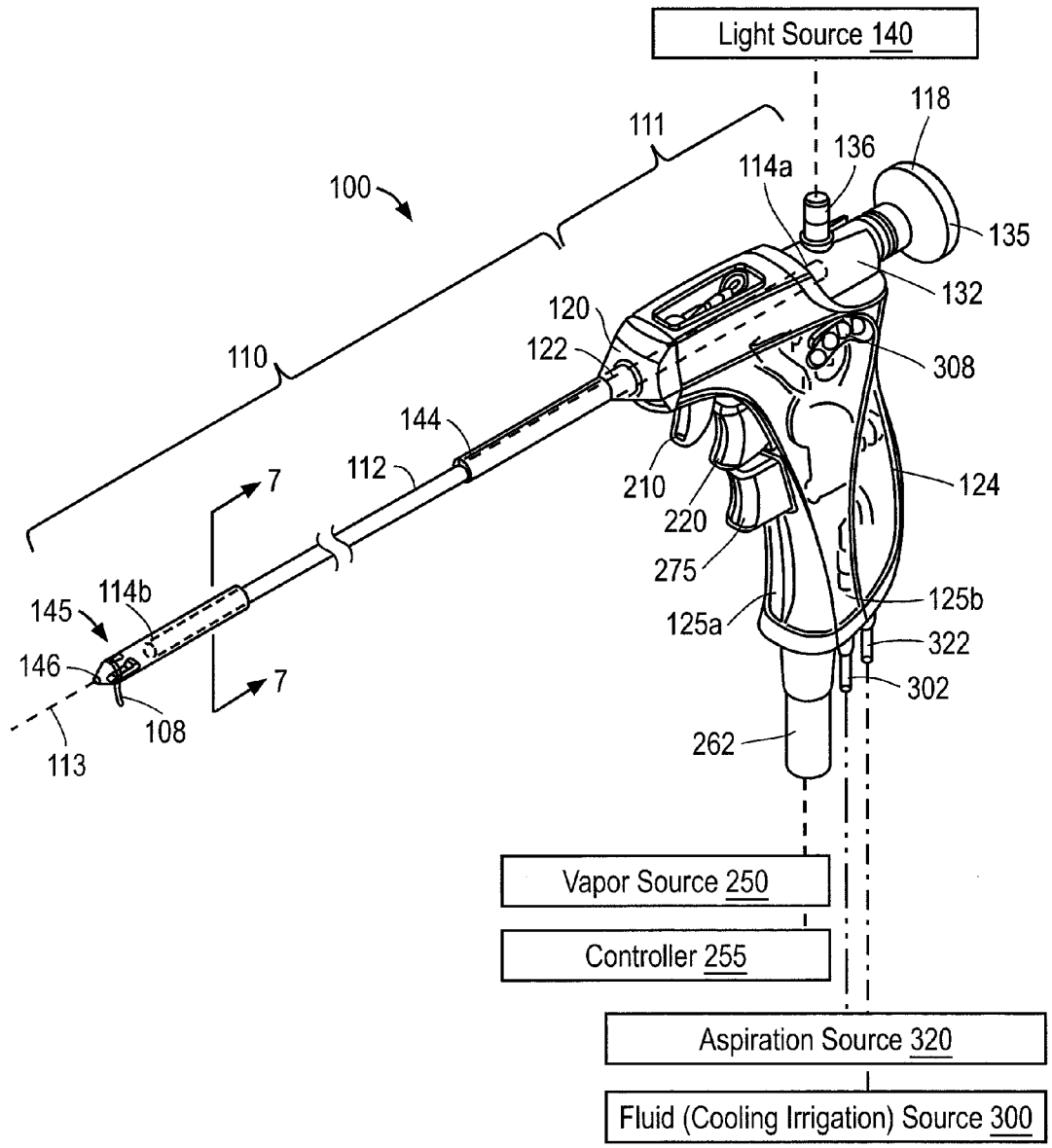
FIG. 4 is a perspective view of a probe corresponding to the invention.
Figure 5:
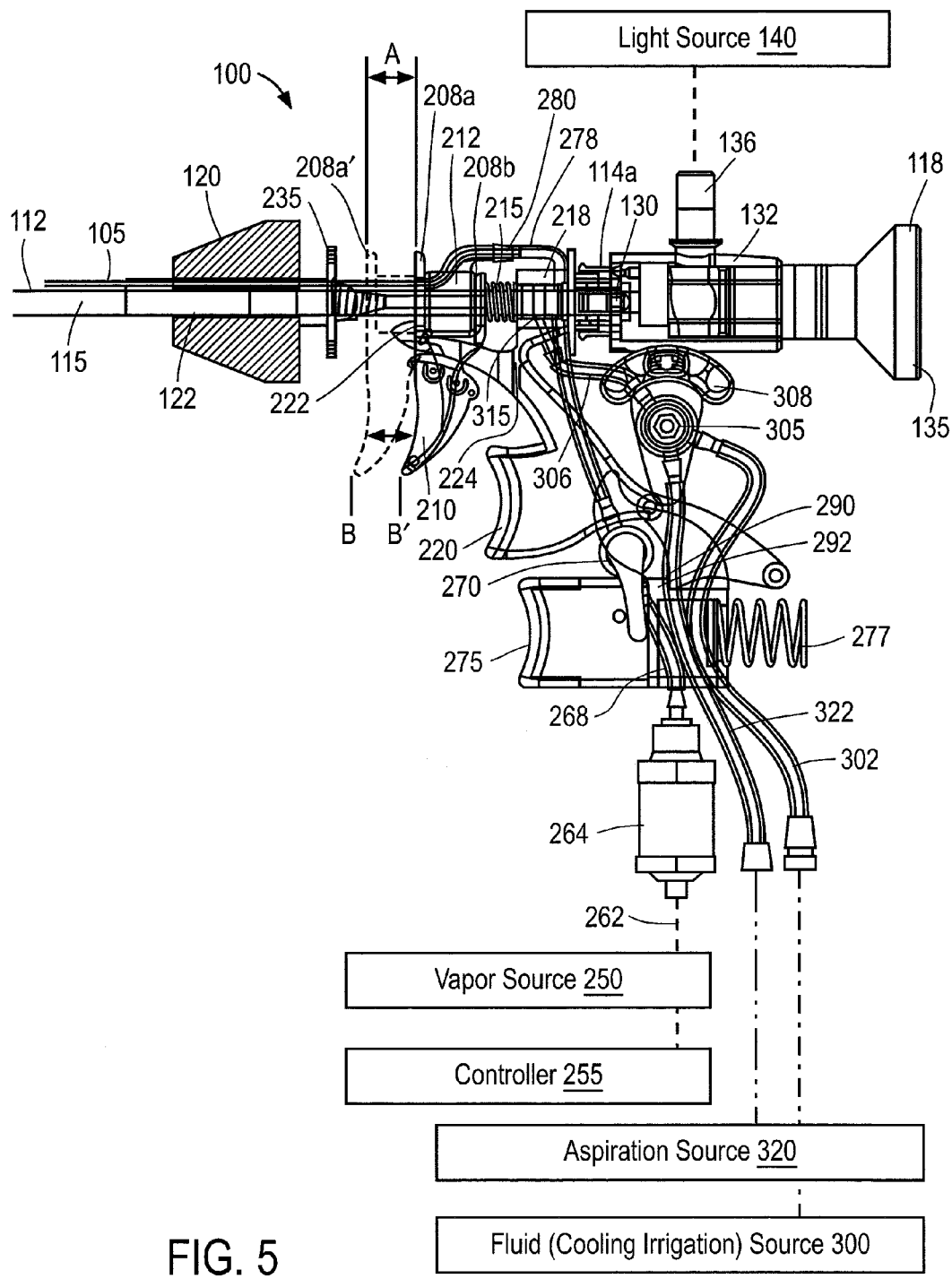
FIG. 5 is a view of components within a handle portion of the probe of FIG. 4.
Figure 6:
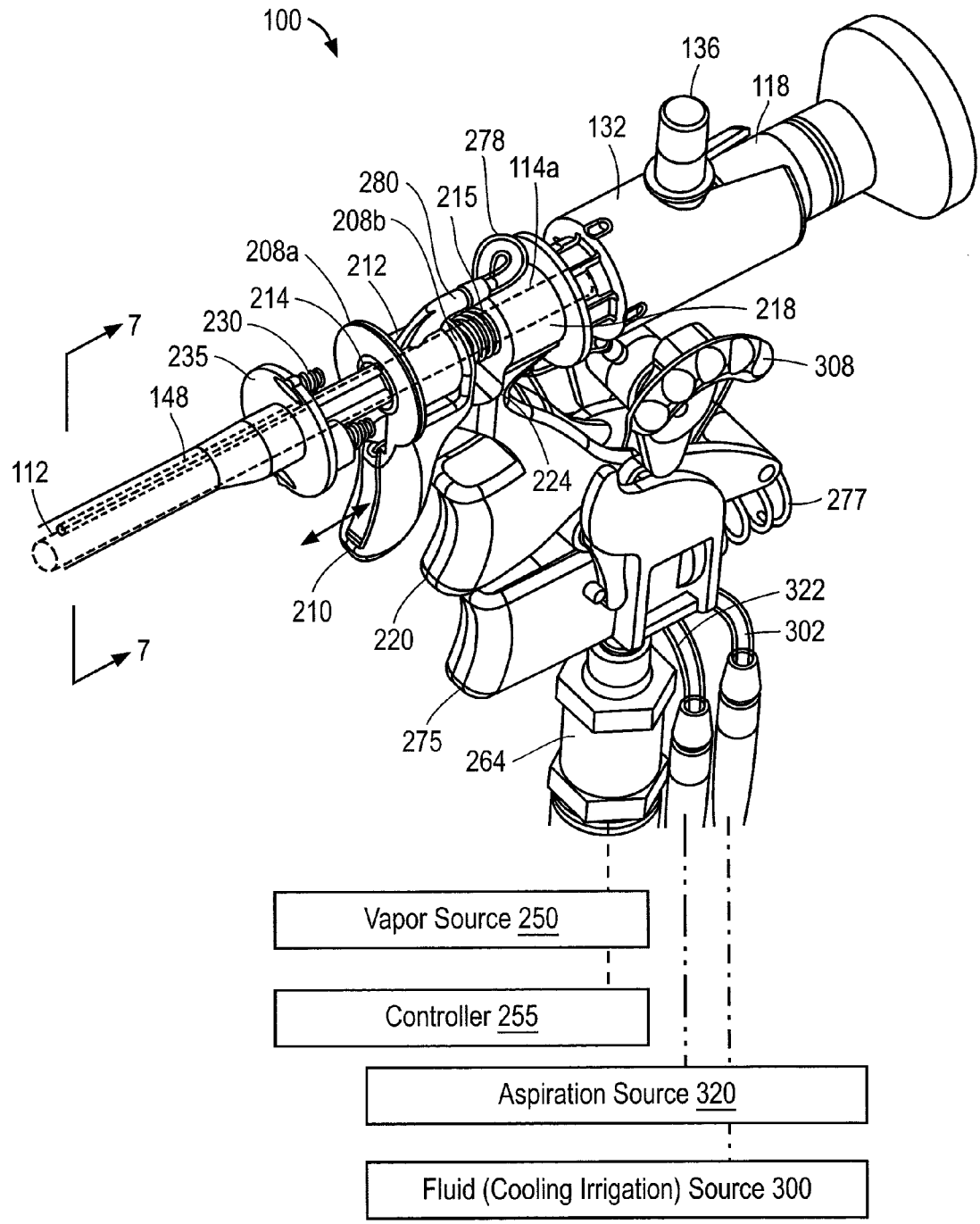
FIG. 6 is another view of components within a handle portion of the probe of FIG. 4.

FIGS. 4, 5 and 6 depict one embodiment of probe 100 of the system of the invention that is adapted for trans-urethral access to the prostate and which provides viewing means to view the urethra as the probe in navigated to a site in the interior of the patient's prostate. The probe 100 further carries an extendable and retractable microcatheter member 105 (FIGS. 5-6) having a distal tip portion 108 (FIG. 4) that can be penetrated into precise targeted locations in prostate lobes to ablate targeted tissue volumes.

Handle and Introducer Portion

In FIG. 4, it can be seen that probe 100 has an elongate introducer portion 110 for insertion into the urethra and a handle portion 111 for gripping with a human hand. The key structural component of introducer portion 110 comprises a rigid introducer sleeve or extension sleeve 112 extending along longitudinal axis 113 with proximal end 114a and distal end 114b. The bore 115 in the rigid extension sleeve extends along longitudinal axis 116. In one embodiment, referring to FIGS. 4 and 5, the extension sleeve 112 comprises a thin-wall stainless steel tube with bore 115 dimensioned to receive a commercially available viewing scope or endoscope 118. The schematic cut-away view of FIG. 5 shows structural bulkhead 120 coupled to a medial portion 122 of extension sleeve 112. The structure or bulkhead 120 comprises the structural member to which the molded handle having pistol grip 124, and more particularly the right- and left-side mating handle parts, 125a and 125b, are coupled (FIG. 4). The bulkhead can be a plastic molded part that can be fixed to sleeve 112 or rotationally coupled to sleeve 112.

Figure 7:
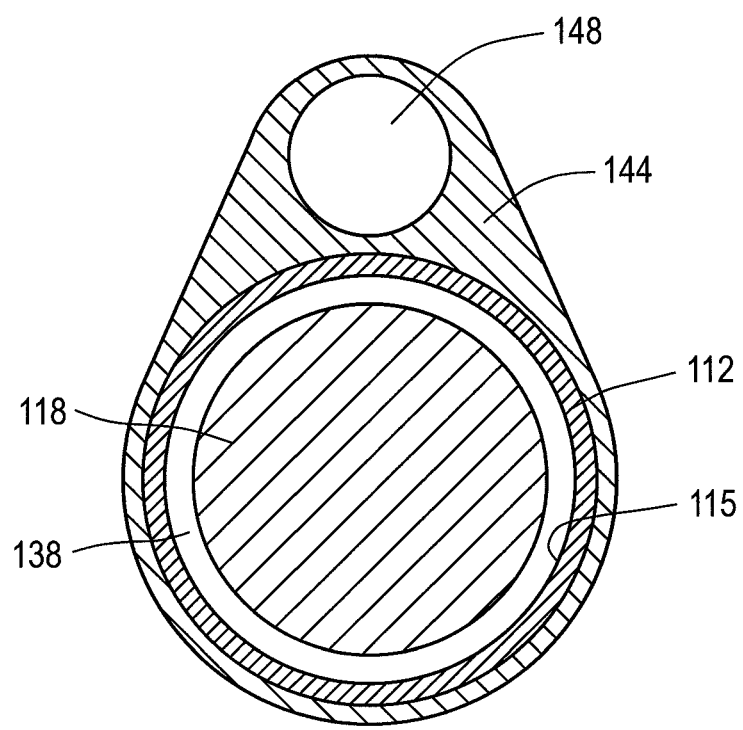
FIG. 7 is a cross sectional view of a probe.

Referring to FIGS. 5-6, in which the molded handle left and right sides are not shown, it can be seen that bore 115 in sleeve 112 has a proximal open end 130 into which the endoscope 118 can be inserted. The proximal end portion 114a of extension sleeve 112 is coupled to an adapter mechanism 132 that releasably engages the endoscope 118 and rotationally aligns the scope 118 with the introducer portion 110. The endoscope 118 has a proximal viewing end 135 and light connector 136 extending outward from the viewing end 136 for coupling a light source 140 to the endoscope. FIG. 7 illustrates that bore 115 in sleeve 112 has a diameter ranging from about 2 to 5 mm for accommodating various endoscopes 118, while at the same time providing an annular space 138 for allowing an irrigation fluid to flow through bore 115 and outwardly from the introducer portion.

Figure 8:
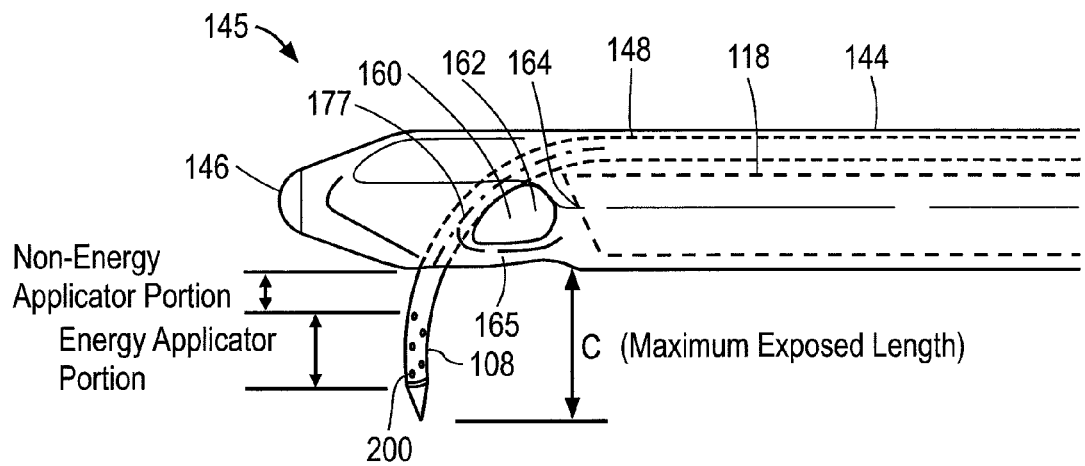
FIG. 8 is a side view of a microcatheter or needle of a probe.
Figure 9:
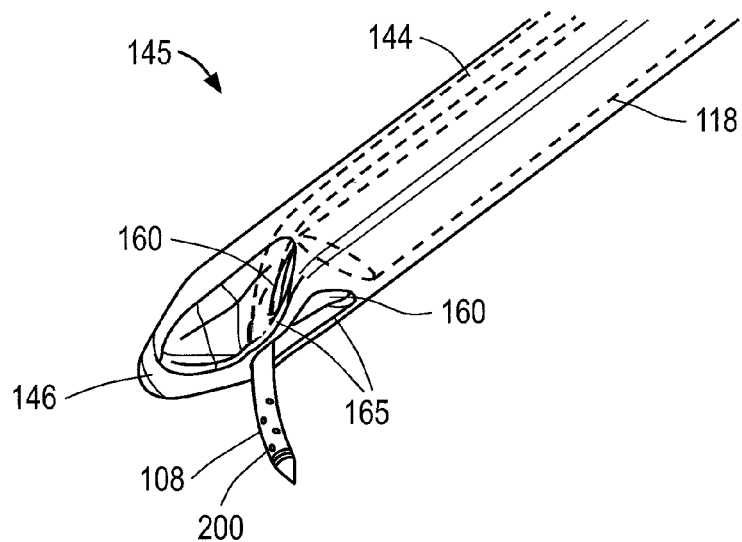
FIG. 9 is a side elevation view of the microcatheter or needle of the probe of FIG. 4 showing its dimensions and vapor outlets.

In one embodiment of system 100, referring to FIGS. 5-8, the extendable-retractable microcatheter 105 comprises a thin-wall flexible polymer tube with a sharp tip that is axially slidable in a passageway 148 in the introducer portion 110. FIGS. 4, 7 and 9 show that the introducer portion 110 comprises an elongate introducer body 144 of plastic or another suitable material that surrounds extension sleeve 112. The introducer body 144 extends to a distal working end portion 145 having a blunt nose or tip 146 for advancing through the urethra. The elongate introducer body 144 is further configured with passageway 148 that accommodates the microcatheter member 105 as will be described below. Referring to FIGS. 8-9, the distal end portion 145 of the introducer body 144 is configured with openings 160 that open to central open region 162 that is distal to the distal lens 164 of endoscope 118 that allows for viewing of the urethra through the lens 164 of the endoscope during navigation. The endoscope 118 can have a lens with a 30°, 12.5° or other angle for viewing through openings 160. As can be seen in FIGS. 8-9, the openings 160 have bridge elements 165 therebetween that function to prevent tissue from falling into central open region 162 of the introducer body 144. In FIG. 8, it can be seen that the working end portion 105 of the flexible microcatheter shaft 105 is disposed adjacent to open region 162 and thus can be viewed through the endoscope lens 164.

Microcatheter and Spring-Actuator

Figure 1:
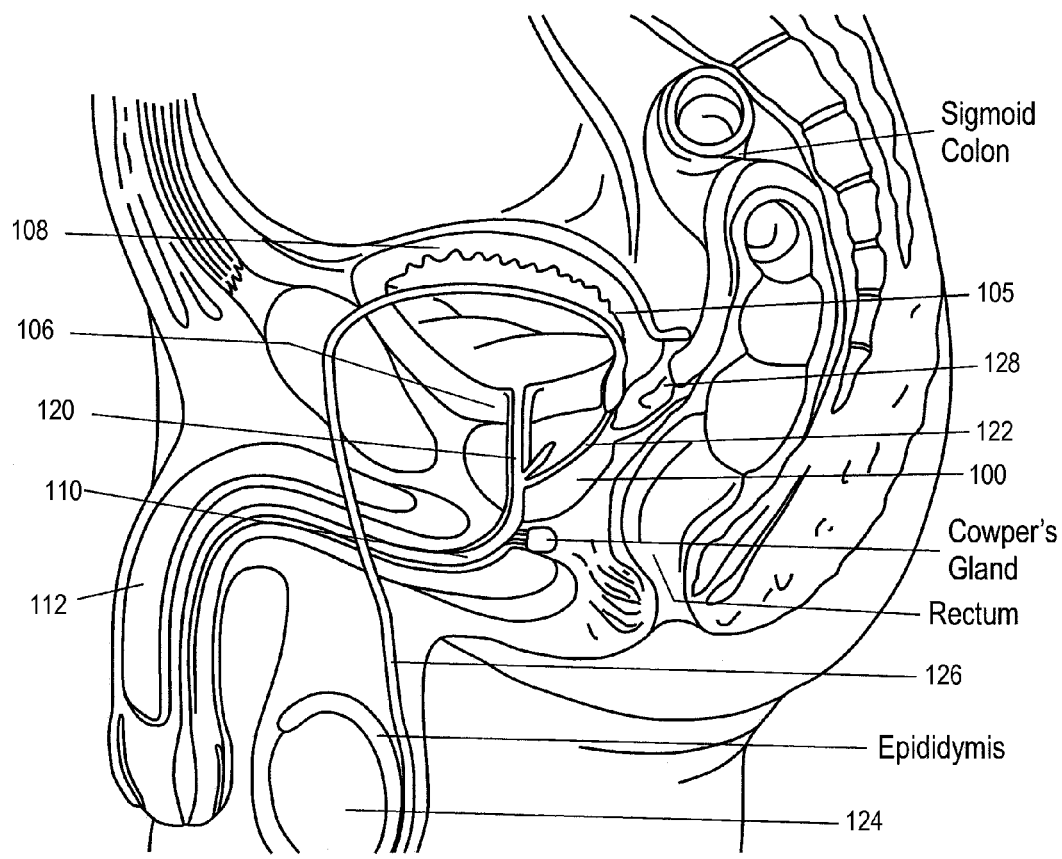
FIG. 1 is a sectional schematic view the male urogenital anatomy.
Figure 2C:
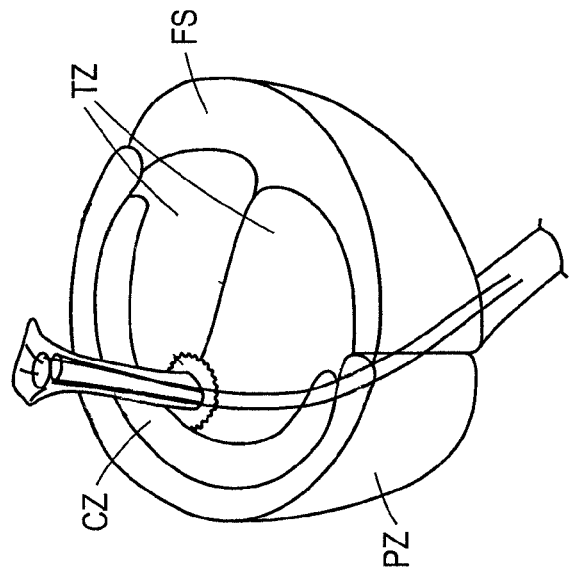
FIG. 2A-2C are views of a patient's prostate showing zones of prostate tissue.
Figure 2B:
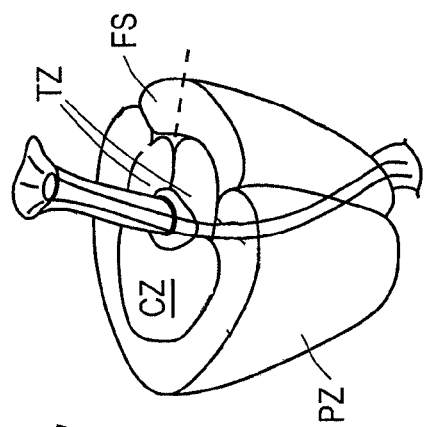
Figure 2A:
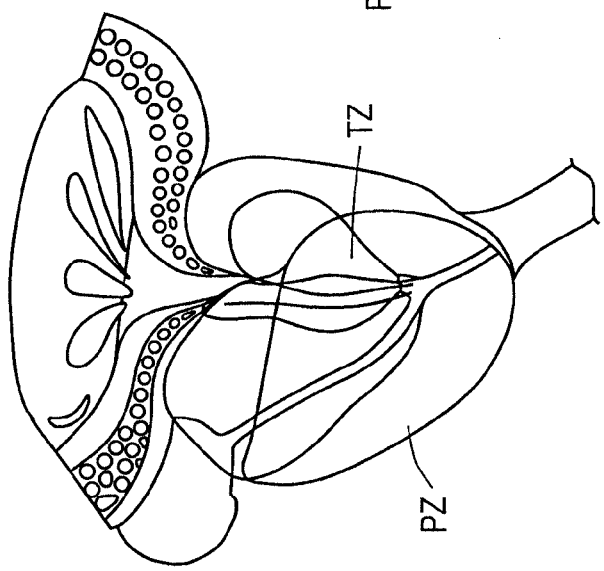
Figure 10:
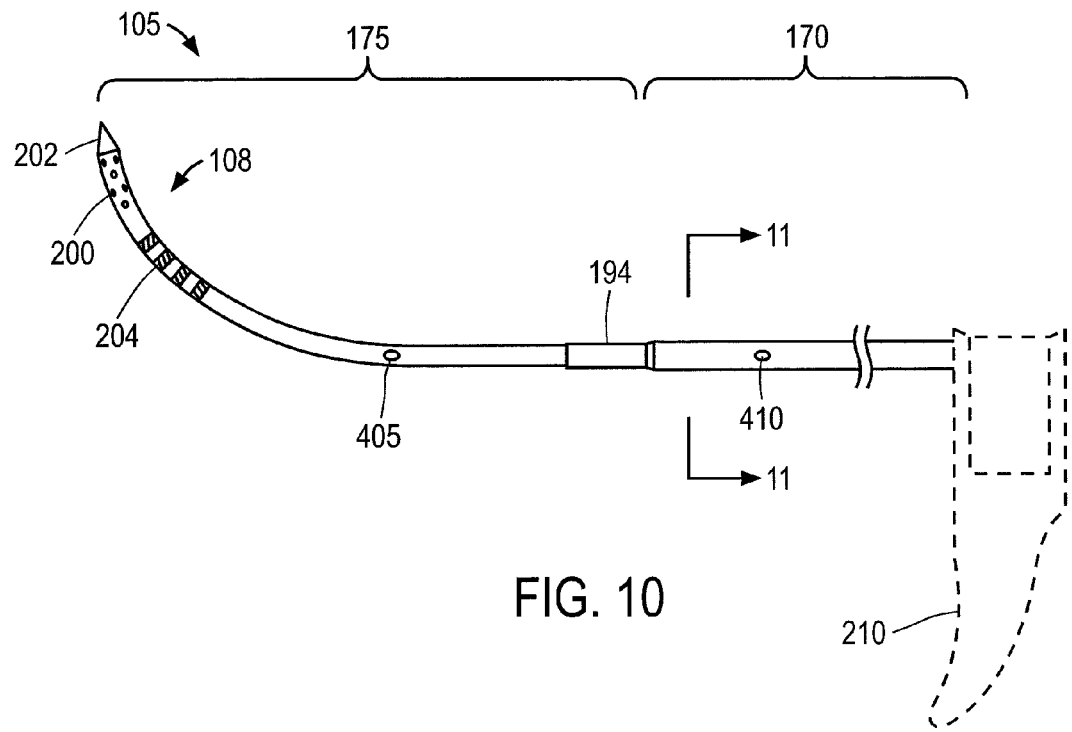
FIG. 10 is another view of the microcatheter of FIG. 9.
Figure 11:
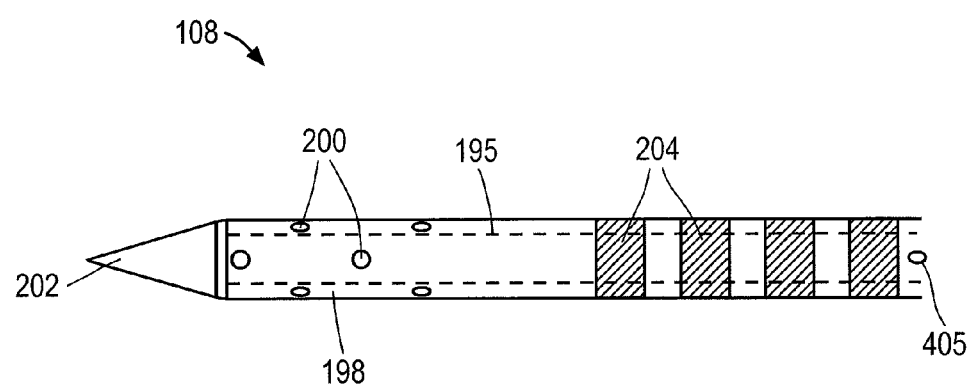
FIG. 11 is another view of a distal portion of the microcatheter of FIG. 10.
Figure 12:
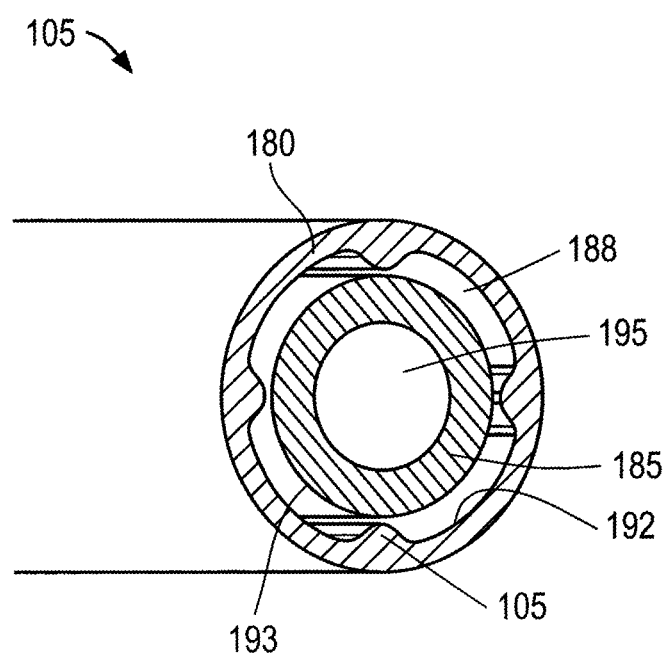
FIG. 12 is a sectional view of the microcatheter of FIG. 10 taken along line 11-11 of FIG. 10.

FIGS. 10-11 show the flexible microcatheter member or needle 105 de-mated from the probe 100 to indicate its repose shape. In one embodiment, the microcatheter 105 has a first (proximal) larger cross-section portion 170 that necks down to second (distal) cross-section portion 175 wherein the smaller cross-section portion 175 has a curved repose shape with the curve configured to conform without significant resistance to the contour of the curved axis 177 of the path followed by the working end 108 of the microcatheter 105 as it is moved from its non-extended position to its extended position as shown in FIGS. 1, 8 and 9. In one embodiment, referring to FIGS. 10-12, the microcatheter's first cross section portion 170 comprises a thin wall outer sleeve 180 that is concentrically outward from inner microcatheter tube 185 that extends the length of the microcatheter member 105. As can be seen in FIG. 12, the outer sleeve 180 provides a thermally insulative air gap 188 around inner tubular member 185. In one embodiment shown depicted in FIG. 12, the outer sleeve 180 is configured with intermittent protrusions 190 that maintain the air gap 188 between the inner surface 192 of outer sleeve 180 and outer surface 193 of inner microcatheter tube. FIG. 9 shows that the outer sleeve 180 has necked down portion 194 that is bonded to inner microcatheter tube 185 by any suitable means such as ultrasonic bonding, adhesives or the like. Referring back to FIG. 10, both the outer sleeve 180 and inner tubular member can comprise a high-temperature resistant polymer such as Ultem® that is suited for delivering a high temperature vapor as will be described below. In one embodiment, the microcatheter tube 185 has an outside diameter of 0.050" with an interior lumen 195 of approximately 0.030". Referring to FIGS. 8-9, one embodiment of working end portion 108 for delivering vapor media to tissue has a thin wall 198 with a plurality of outlet ports 200 therein that are configured for emitting a vapor media into tissue as will be described below. The outlet ports can range in number from about 2 to 100, and in one embodiment consist of 12 outlets each having a diameter of 0.008" in six rows of two outlets with the rows staggered around the working end 108 as shown in FIG. 10. In one embodiment shown in FIGS. 10-11, the distalmost tip 202 of the microcatheter tube 185 has a sharpened conical configuration that can be formed of the plastic material of tube 185. As will be described below, it has been found that a polymeric needle and needle tip 202 is useful for its thermal characteristics in that its heat capacity will not impinge on vapor quality during vapor delivery.

FIGS. 10-11 further illustrate that the distal tip portion 108 of microcatheter tube 185 has at least one marking 204 that contrasts with the color of the microcatheter tube 185 that is adapted for viewing through lens 164 of the endoscope 118. In one embodiment, the distal tip portion has a series of annular marks 204 of a first color that contrasts with second color of tube 185, wherein the marks are not visible through the endoscope lens 164 when the microcatheter tube 185 is in the non-extended position. After the microcatheter tube 185 is extended into tissue, the marks are visible through the lens 164 which indicates the tube 185 has been extended into tissue.

Returning now to FIGS. 5 and 6, the cut-away view of the handle portion 111 shows the microcatheter member 105 and associated assemblies in the non-extended position. FIG. 5 shows flanges 208a and 208b of cocking actuator 210 are disposed on either side of actuator collar 212 that is coupled to proximal end 214 of the slidable microcatheter member 105. As can be understood from FIG. 5, the downward-extending cocking actuator 210 is adapted to cock the flanges 208a, 208b and microcatheter 105 to a cocked position which corresponds to the non-extended position of the microcatheter 105. In FIG. 5, the actuator 210 is shown in a first position B (phantom view) and second positions B' following actuation with an index finger to thus cock the microcatheter member 105 to the second releasable non-extended position (or cocked position) B' from its extended position B. The flange 208a and actuator 210 is further shown in phantom view in the released position indicated at 208a'. In FIG. 5, the flanges 208a, 208b and associated assemblies are configured for an axial travel range indicated at A that can range from about 8 mm to 15 mm which corresponds to the travel of the microcatheter 105 and generally to the tissue-penetration depth. In the embodiment of FIG. 5, the flanges 208a, 208b and microcatheter member 105 are spring-actuatable to move from the non-extended position to the extended position by means of helical spring 215 disposed around sleeve 112. As can be seen in FIG. 5, the spring 215 is disposed between the slidable flange 208b and trigger block 218 that comprises a superior portion of the release trigger 220 which is adapted to release the microcatheter 105 from its cocked position.

FIG. 5 further illustrates the release trigger 220 releasably maintaining the flange 205a and microcatheter 105 in its cocked position wherein tooth portion 222 of the trigger 220 engages the lower edge of flange 205a. It can be understood from FIG. 5 that the release trigger 220 is configured to flex or pivot around living hinge portion 224 when trigger 220 is depressed in the proximal direction by the physician's finger actuation. After actuation of trigger 220 and release of the microcatheter 105 to move distally, the axial travel of the assembly is configured to terminate softly rather than abruptly as flange 208a contacts at least one bumper element 230 as depicted in FIG. 6. The bumper elements 230 can comprise any spring or elastomeric element, and in FIG. 6 are shown as an elastomer element housed in a helical spring, which serve to cushion and dampen the end of the travel of the spring-driven microcatheter assembly. The bumper elements 230 are coupled to flange 235 which in turn is configured to be fixed between right- and left-side handle parts 125a and 125b (FIG. 4).

Now turning to the energy-delivery aspect of the system, a vapor source 250 is provided for delivering a vapor media through the microcatheter member 105 to ablate tissue. The vapor source can be a vapor generator that can deliver a vapor media, such as water vapor, that has a precisely controlled quality to provide a precise amount of thermal energy delivery, for example measured in calories per second. Descriptions of suitable vapor generators can be found in the following U.S. patent applications: application. Ser. Nos. 11/329, 381; 60/929,632; 61/066,396; 61/068,049; 61/068,130; 61/123,384; 61/123,412; 61/126,651; 61/126,612; 61/126, 636; 61/126,620 all of which are incorporated herein by reference in their entirely. The vapor generation system also can comprise an inductive heating system similar to that described in Application Nos. 61/123,416, 61/123,417, 61/126,647. The system further includes a controller 255 that can be set to control the various parameters of vapor delivery, for example, the controller can be set to delivery vapor media for a selected treatment interval, a selected pressure, or selected vapor quality.

Referring to FIG. 5, in one embodiment, the vapor source 250 is remote from the handle 124 and vapor media is carried to the handle by a flexible conduit 262 that couples handle and check valve 264 therein. In one embodiment, vapor can be re-circulating in conduit 262 until a solenoid in the vapor source is actuated to cause the vapor flow to thus provide an increased fluid pressure which opens the check valve 265 and allows the vapor media to flow through flexible tube 268 to valve 270 that can be finger-actuated by trigger 275. In one embodiment depicted in FIG. 5, the trigger 275 is urged toward a non-depressed position by spring 277 which corresponds to a closed position of valve 270. The trigger 275 also can be coupled by an electrical lead (not shown) to controller 255. Thus, actuating the trigger 275 can cause the controller to actuate a solenoid valve in the vapor generator to cause vapor flow through the relief valve. As a safety mechanism, the valve 270 in the handle is opened only by its actuation to thus permit the flow of vapor media through flexible tube 278 which communicates with inflow port portion 280 of collar 212 which in turn communicates with the lumen 195 in the microcatheter 105. Thus, FIG. 5 illustrates the flow path and actuation mechanisms that provide vapor flow on demand from the vapor source 250 to the vapor outlets 200 in working end 108 of the microcatheter 105.

As can be seen in FIG. 5, the handle can also provide an interlock mechanism that prevents the actuation of vapor flow if the microcatheter release trigger is in the cocked position, wherein edge portion 292 coupled to release trigger 220 can engage notch 294 in trigger 275 to prevent depression of said trigger 275.

Still referring to FIG. 5, one embodiment of the system includes a fluid irrigation source 300 that is operatively couple to the bore 115 in extension member 112 to deliver a fluid outward from the bore 115 to the open region 162 of the probe working end 145 (see FIG. 8). As can be seen in FIG. 7, the bore 115 is dimensioned to provide a space 138 for fluid irrigation flow around the endoscope 118. In FIG. 5, it can be seen that fluid source 300, which can be a drip bag or controlled pressure source of saline or another fluid, is detachably coupled to tubing 302 in the handle which extends to a valve 305 that can be thumb-operated from actuators 308 on either side of the handle. The thumb actuator 308 can also control the rate of flow of the irrigation fluid by moving the actuator 308 progressively forward, for example, to open the valve more widely open. The fluid flows from valve 305 through tube 312 to a port or opening 315 in the extension sleeve 112 to thus enter the bore 115 of the sleeve.

FIG. 5 further depicts an aspiration source 320 operatively coupled to tubing 322 in the handle 124 which also can be actuated by valve 305 wherein the thumb actuator 308 can be rocked backwardly to allow suction forces to be applied through the valve 305 to tubing 312 that extends to port 315 in the extension member—which is the same pathway of irrigation flows. Thus, suction or aspiration forces can withdraw fluid from the working end of the device during a treatment.

Another aspect of one embodiment of probe 100 corresponding to the invention, referring to FIGS. 4, 5, 6 and 8, is the orientation of the microcatheter or needle 105 as it exits the working end 145 relative to the orientation of the pistol grip 124 of the handle portion 111. In a method use further described below, the introducer will typically be introduced through the urethra with the pistol grip in a "grip-downward" orientation GD (FIG. 13A) with the pistol grip 126 oriented downwardly which comfortable for the physician. The treatment will typically include rotationally re-orienting the probe as indicated in FIG. 13A so that the microcatheter or needle 105 can be penetrated into prostate lobes at 90° to about 135° relative to a grip-downward position. FIGS. 13A and 13B are schematic head-on views of the probe 100 in a prostate with the microcatheter 105 deployed showing the orientation of the handle pistol grip 124, the deployed microcatheter 105 and the connector endoscope 136 which indicate the rotational orientation of the endoscope 118 and thus the orientation of the camera image on the monitor. As can be seen in FIGS. 4-6, the assembly of the introducer 110, microcatheter 105 and endoscope 118 is rotatable within the handle within flanges 235A and 235B. In one embodiment, the system has click-stops at various angles, such as every 15° between 75° and 135° relative to the grip-downward orientation GD of FIG. 13A. Thus FIGS. 13A-13A and 14A-14B depict optional methods that the surgeon may use.

FIGS. 13A and 13B depict the physician locking all components of the probe 100 in a single rotational orientation, and simply using his rotating his hand and pistol grip 124 to a selected orientation of greater that 90° from the grip-down position GD, then releasing the microcatheter 105 to penetrate into the prostate lobe. After actuating the vapor delivery trigger, the vapor ablates are region indicted at 400. It can be appreciated that the endoscope 118 is rotated so that the image on the monitor is also rotated. Thereafter, the physician rotates the probe as depicted in FIG. 13B to treat the other prostate lobe. This method may be preferred by physicians that are familiar with anatomical landmarks, opt for simplicity and are accustomed to viewing an image on the monitor which is rotated relative a true vertical axis of the patient anatomy.

FIGS. 14A and 14B depict the physician utilizing the rotational feature of the probe and maintaining the handle pistol grip 124 in the grip-down orientation GD and rotating the introducer 110 and microcatheter 105 to the appropriate angles to treat the first and second lobes of the prostate. This method again is suited for physicians that are familiar with anatomical landmarks and are accustomed to viewing a rotated image on the monitor in the OR.

FIGS. 15A and 15B depict the physician utilizing another embodiment of a probe to treat the two prostate lobes. In the embodiment of FIGS. 5-6, it can be seen that the endoscope 118 is locked in rotational orientation with introducer 110 and the microcatheter 105—but not with the handle pistol grip. It can easily be understood a probe can be made that allows rotational adjustment between the introducer 110 and microcatheter 105 relative to the handle pistol grip 124—but that provided a bracket that rotationally locks the endoscope 118 to the handle pistol grip 124. FIGS. 15A-15B depict the use of such an embodiment, wherein the physician can maintain the handle pistol grip 124 in the grip-down orientation GD and then rotates only the introducer 110 and microcatheter 105. In this embodiment, the image on the monitor will remain vertical instead of rotated, which may be preferred by physicians accustomed to laparoscopy in which images are not rotated on the monitor when instruments are manipulated.

In another aspect of the invention, referring to FIGS. 10-11, the microcatheter 105 carries a temperature sensor or thermocouple 405 at a distal location therein, for example as indicated in FIG. 10. The thermocouple is operatively connected to controller 255 to control vapor delivery. In one embodiment, an algorithm reads an output signal from the thermocouple 405 after initiation of vapor delivery by actuation of trigger 275, and in normal operation the thermocouple will indicate an instant rise in temperature due to the flow of vapor. In the event, the algorithm and thermocouple 405 do not indicate a typical rise in temperature upon actuation of trigger 275, then the algorithm can terminate energy delivery as it reflects a system fault that has prevented energy delivery.

In another embodiment, referring again to FIGS. 10-11, the microcatheter 105 can carry another temperature sensor or thermocouple 410 in a portion of microcatheter 105 that resides in passageway 148 of the introducer body 144. This thermocouple 410 is also operatively connected to controller 255 and vapor source 250. In one embodiment, an algorithm reads an output signal from thermocouple 410 after initiation of vapor delivery and actuation of actuator 308 that delivers an irrigation fluid from source 300 to the working end 145 of the probe. The delivery of irrigation fluid will maintain the temperature in the region of the thermocouple at a predetermined peak level which will not ablate tissue over a treatment interval, for example below 55° C., below 50° C. or below 45° C. If the temperature exceeds the predetermined peak level, the algorithm and controller can terminate vapor energy delivery. In another embodiment, a controller algorithm and modulate the rate of cooling fluid inflows based on the sensed temperature, and/or modulate the vapor flow in response to the sensed temperature. In an alternative embodiment, the thermocouple 410 can be in carried in a portion of introducer body 144 exposed to passageway 148 in which the microcatheter resides.

Method of Use

Figure 16A:
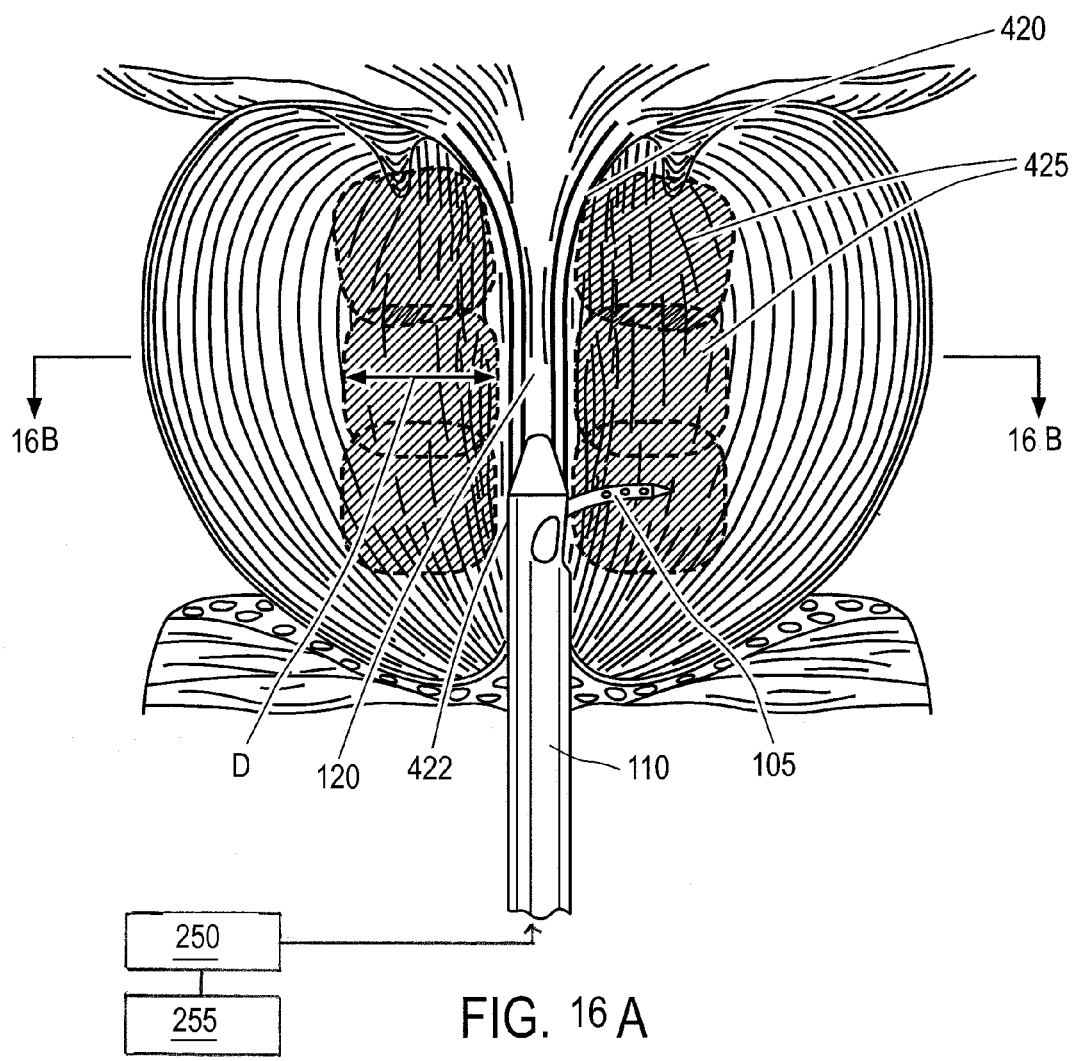
FIG. 16A is a longitudinal sectional schematic view showing a method of the invention in treating a prostate for BPH.
Figure 16B:
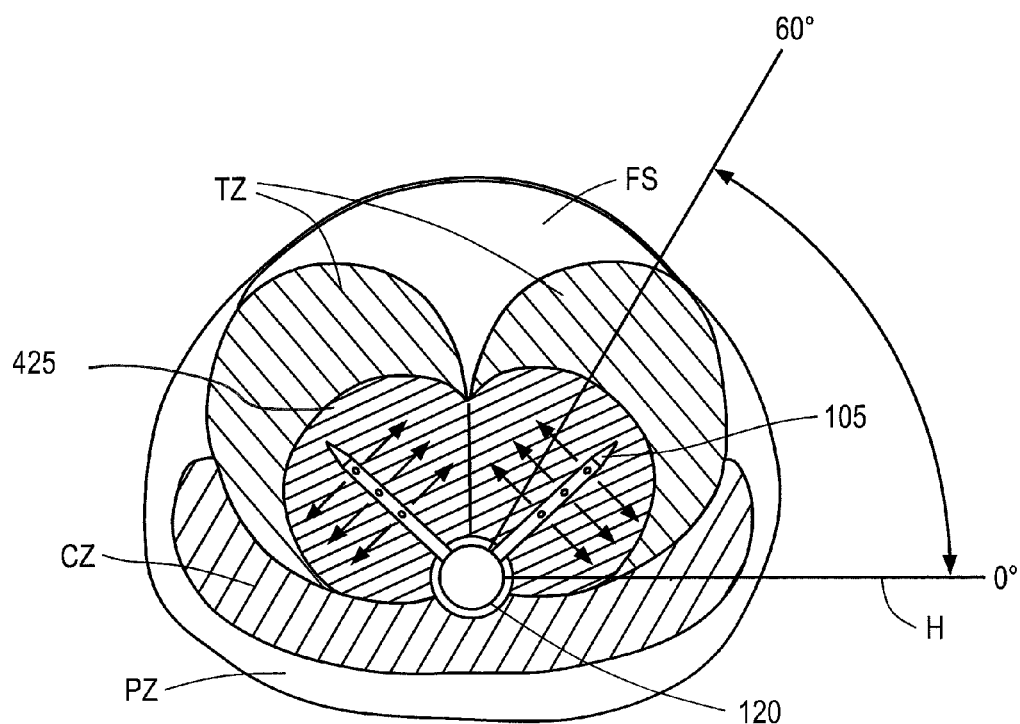
FIG. 16B is a transverse sectional view of the prostate of FIG. 16A.

Referring to FIGS. 16A and 16B, the device and method of this invention provide a precise, controlled thermal ablative treatment o tissue in first and second lateral prostate lobes (or right- and left-side lobes), and additionally an affected median lobe in patients with an enlarged median lobe. In particular, the ablative treatment is configured to ablate stromal or smooth muscle tissue, to ablate alpha adrenergic (muscle constriction) receptors, and to ablate sympathetic nerve structures. More in particular, the method of ablative treatment is configures to target smooth muscle tissue, alpha adrenergic receptors, and sympathetic nerve structures parallel to the prostatic urethra between the bladder neck region 420 and the verumontanum region 422 as depicted in FIGS. 16A-16B. The targeted ablation regions 425 have a depth indicated at D in FIGS. 16A-16B that is less than 2 cm from the prostatic urethra 120, or less than 1.5 cm. Depending on the length of the patient's prostatic urethra 120, the number of ablative energy deliveries can range from 2 to 4 and typically is 2 or 3.

In a method of use, the physician would first prepare the patient for trans-urethral insertion of the extension portion 110 of the probe 100. In one example, the patient can be administered orally or sublingually a mild sedative orally or sublingually such as Valium, Lorazepam or the like from 15-60 minutes before the procedure. Of particular interest, it has been found that prostate blocks (injections) or other forms of anesthesia are not required due to lack of pain associated with an injection of a condensable vapor. The physician then actuates the needle-retraction actuator 210, for example with an index finger, to retract and cock the microcatheter 105 by axial movement of the actuator (see FIGS. 4-6). By viewing the handle 124, the physician can observe that the microcatheter 105 is cocked by the axial location of trigger 210. A safety lock mechanism (not shown) can be provided to lock the microcatheter 105 in the cocked position.

Next, the physician advances the extension portion 110 of the probe 100 trans-urethrally while viewing the probe insertion on a viewing monitor coupled to endoscope 118. After navigating beyond the verumontanum 422 to the bladder neck 420, the physician will be oriented to the anatomical landmarks. The landmarks and length of the prostatic urethra can be considered relative to a pre-operative plan based on earlier diagnostic ultrasound images or other images, such as MRI images.

Figure 17:
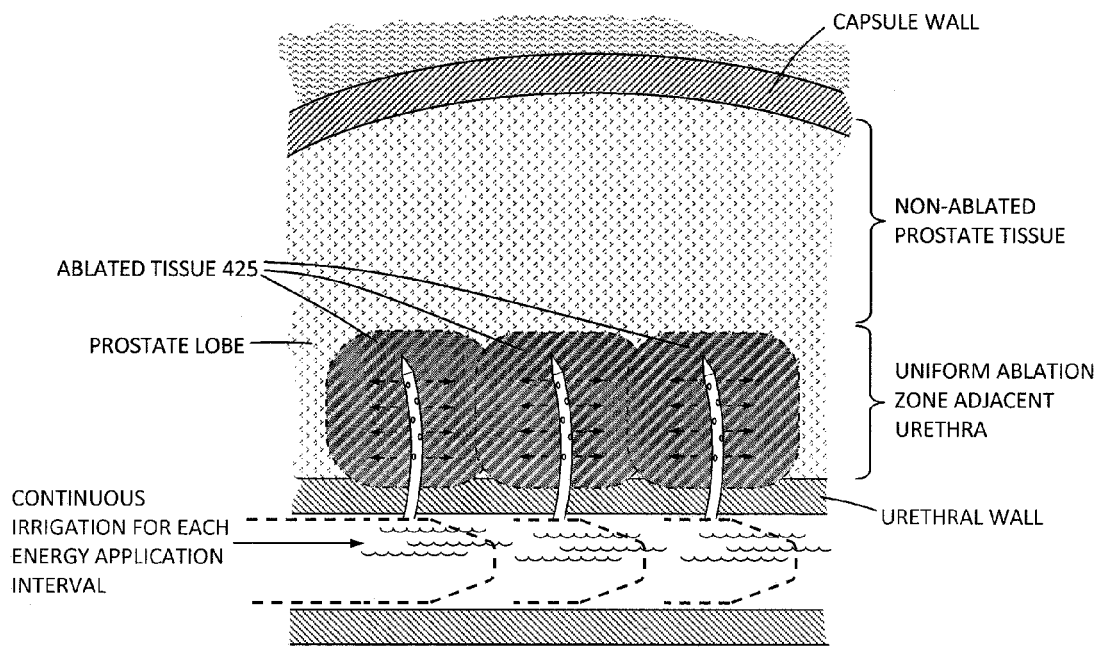
FIG. 17 is another longitudinal sectional view showing ablation zones in the method of treating a prostate for BPH.

The physician can rotate the microcatheter-carrying probe about its axis to orient the microcatheter at an angle depicted in FIG. 13A to treat a first lobe. Thereafter, the treatment included cocking and releasing the microcatheter followed by vapor delivery, the moving and repeating the vapor injection for a total of three vapor injections in each lobe. FIG. 17 is a schematic view of a method the invention wherein three penetrations of the microcatheter 105 are made sequentially in a prostate lobe and wherein energy delivery is provided by vapor energy to produce slightly overlapping ablations or lesions to ablate the smooth muscle tissue, alpha adrenergic receptors, and sympathetic nerve structures in a region parallel to the prostatic urethra. The method of the invention, when compared to prior art, reduces the burden of ablated tissue and thus lessens the overall inflammatory response leading to more rapid tissue resorption and more rapid clinical improvement.

Figure 18:
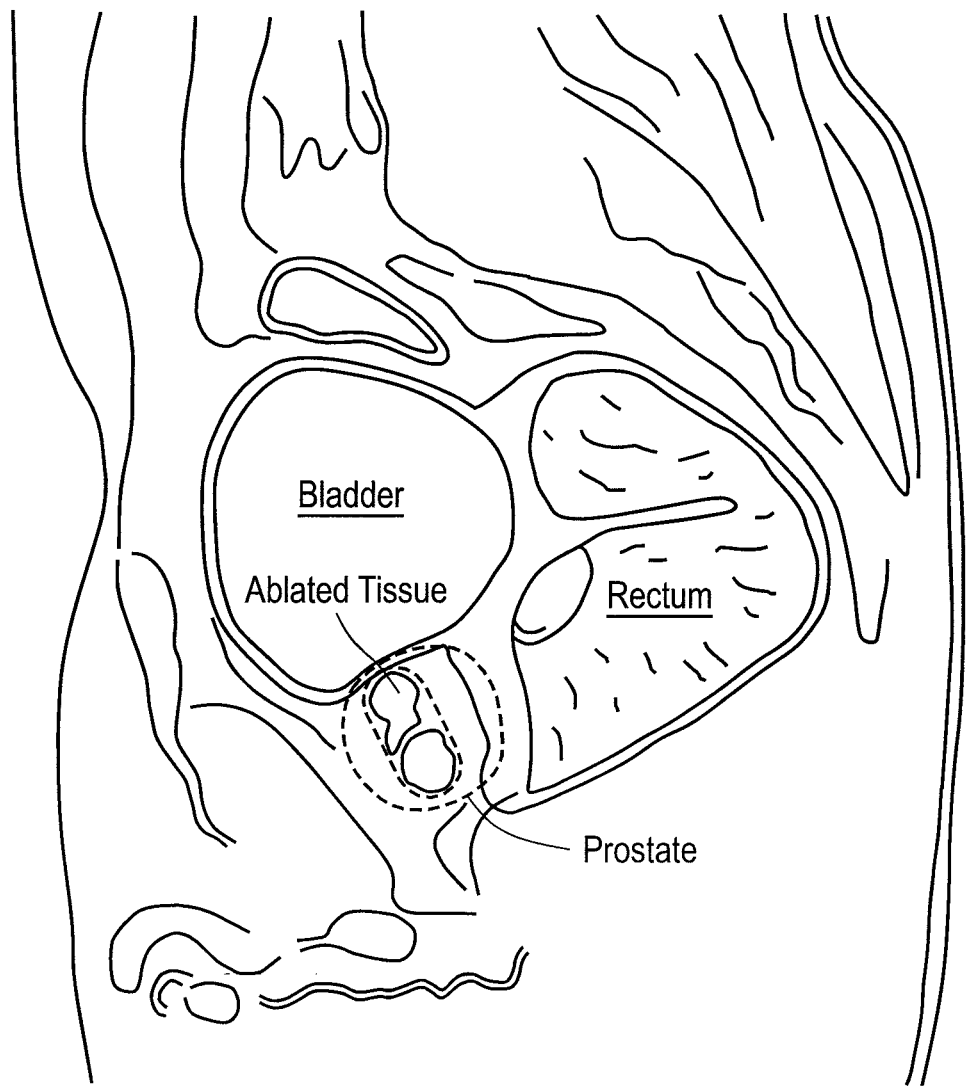
FIG. 18 is an MRI from a patient 1 week after a treatment as indicated schematically in FIGS. 16A-17.

FIG. 18 is a sagittal MRI image of an exemplary BPH treatment of a patient 1 week following the procedure, in which the treatment included the following steps and energy delivery parameters. The patient's prostate weighed 44.3 gms based on ultrasound diagnosis. Amparax (Lorazepam) was administered to the patient 30 minutes before the procedure. In the treatment of the patient in FIG. 18, each treatment interval consisted of 10 seconds of vapor delivery at each of six locations (3 injections in each lobe). Thus, the total duration of actual energy delivery was 60 seconds in the right and left prostate lobes. The energy delivered was 6 cal/sec, or 60 cal. per treatment location 425 (FIG. 16A) and a total of 360 calories in total to create the ablation parallel to the prostatic urethra, which can be seen in the MRI of FIG. 18. In the patient relating to the MRI image of FIG. 18, the median lobe was also treated with a single 10 second injection of vapor, or 50 calories of energy. The vapor can be configured to delivery energy in the range of 5 to 10 cal/sec.

Figure 3A:
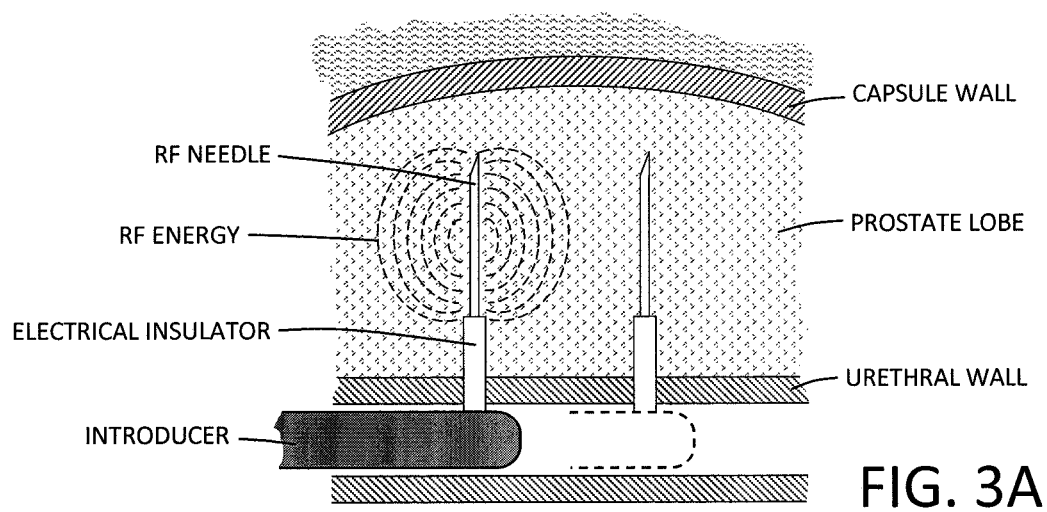
FIG. 3A is a sectional view of a normal prostate gland.
Figure 3B:
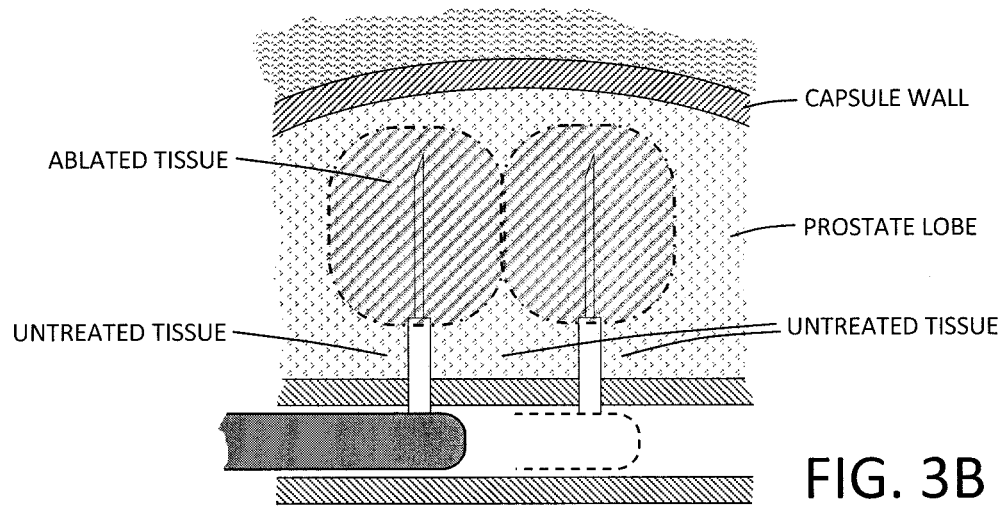
FIG. 3B is a sectional view of a prostate gland with BPH.

By comparing the method of the present invention (FIG. 17) with the prior art (FIGS. 3A-3B), it can be understood the method and apparatus of the present invention is substantially different than the prior art. FIG. 3A schematically depicts the prior art RF needle that is elongated, typically at about 20 mm in length, which ablates tissue away from the prostatic urethra and does not target tissue close to and parallel to the prostatic urethra. Second, the prior art RF energy delivery methods apply RF energy for 1 to 3 minutes or longer which allows thermal diffusion of effect to reach the capsule periphery, unlike the very short treatment intervals of the method of the present invention which greatly limit thermal diffusion. Third, the prior art RF energy delivery methods do not create a uniform ablation of tissue adjacent and parallel to the prostatic urethra to ablate smooth muscle tissue, alpha adrenergic receptors, and sympathetic nerve structures in a region parallel to the prostatic urethra.

Figure 19:
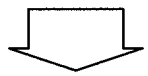
FIG. 19 is a block diagram of a method corresponding to the invention.
Figure 19:
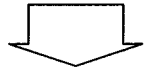

One method corresponding to the invention is shown in the block diagram of FIG. 19, which includes the steps of advancing a probe trans-urethrally to the patient's prostate, extending a energy applicator or microcatheter into prostate lobes in a plurality of locations to a depth of less than 2 cm, and then applying energy at each location to create an ablation zone in a continuous region parallel to at least a portion of the prostatic urethra.

Figure 20:
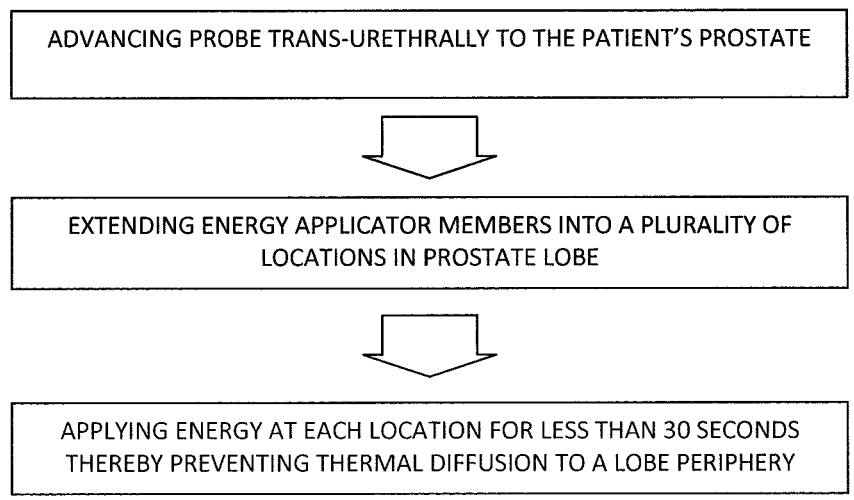
FIG. 20 is a block diagram of another method corresponding to the invention.

Another method of the invention is shown in the block diagram of FIG. 20, which includes the steps of advancing a probe trans-urethrally to the patient's prostate, extending a energy applicator or microcatheter into prostate lobes in a plurality of locations, and applying energy at each location for less than 30 seconds to thereby prevent thermal diffusion to peripheral portions of the lobes.

Figure 21:
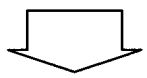
FIG. 21 is a block diagram of another method corresponding to the invention.
Figure 21:
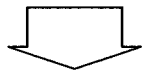

Another method of the invention is shown in FIG. 21, which includes the steps of advancing a probe trans-urethrally to the patient's prostate, extending a energy applicator or microcatheter into prostate lobes in a plurality of locations, and applying energy at each location for a selected interval and irrigating the urethra with a cooling fluid throughout the selected interval of energy delivery. It has been found that such a flow of cooling fluid may be useful, and most important the flow of cooling fluid can be continuous for the duration of the treatment interval since such times are short, for example 10 to 15 seconds. Such a continuous flow method can be used in prior art methods, such as RF ablation methods of FIGS.

3A-3B, since the cooling fluid volume accumulates in the patient's bladder and the long treatment intervals would result in the bladder being filled rapidly. This would lead to additional steps to withdraw the probe, remove the excess fluid and then re-start the treatment.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A vapor therapy system, comprising:
   a shaft adapted to be inserted into a male urethra;
   a vapor delivery needle in the shaft, the needle comprising a vapor exit port;
   a vapor needle deployment mechanism adapted to move a tip of the needle generally transverse to the shaft, wherein the vapor needle deployment mechanism cannot move the vapor delivery needle more than 15 mm from the shaft;
   a vapor source; and
   a vapor delivery actuator adapted to deliver vapor from the vapor source into the vapor delivery needle and out of the vapor exit port.

2. The system of claim 1 wherein the vapor delivery needle is movable between a retracted position in which a distal needle tip is within the shaft and a deployed position in which the distal needle tip extends from the shaft.

3. The system of claim 2 further comprising a needle-retraction actuator adapted to retract the vapor delivery needle into the shaft.

4. The system of claim 1 wherein the vapor delivery needle comprises a non-energy applicator portion that does not include a vapor exit port.

5. The system of claim 4 wherein the non-energy applicator portion is approximately the thickness of the male urethra.

6. The system of claim 1 wherein the vapor delivery needle comprises a flexible polymer tube with sharp tip.

7. The system of claim 1 further comprising an irrigation liquid source and an irrigation passage in the shaft extending from the irrigation liquid source to an irrigation liquid outlet.

8. The system of claim 7 further comprising an irrigation actuator configured to irrigate a cooling fluid from the irrigation liquid source through the irrigation liquid outlet.

9. The system of claim 8 wherein the irrigation actuator is configured to irrigate the cooling fluid when the vapor delivery actuator delivers vapor.

10. The system of claim 8 further comprising an interlock to prevent vapor delivery without irrigation of the cooling fluid.

11. The system of claim 1 further comprising a handle connected to the shaft through an adjustably rotatable connector such that shaft can be rotated with respect to the handle.

12. The system of claim 11 wherein the rotatable connector comprises rotational stops at preset angles.

13. The system of claim 1 further comprising a temperature sensor operably connected to a controller to control vapor delivery based on a sensed temperature.

14. The system of claim 13 wherein the temperature sensor is configured to sense a temperature of the vapor delivery needle.

15. The system of claim 13 wherein the temperature sensor is configured to sense a temperature of the shaft.

16. The system of claim 1 further comprising a vapor delivery interlock adapted to prevent delivery of vapor from the vapor delivery needle unless the vapor delivery needle is deployed.

17. The system of claim 1 wherein the needle deployment mechanism further comprises a limit stop adapted to limit a deployment distance of the needle.

18. The system of claim 1 further comprising a scope bore in the shaft sized to accommodate an endoscope, the scope bore having an opening oriented to permit a user to view a distal end of the vapor delivery needle through the endoscope.

19. A vapor therapy system, comprising:
   a shaft adapted to be inserted into a male urethra;
   a vapor delivery needle in the shaft, the needle comprising a vapor exit port;
   a vapor needle deployment mechanism adapted to move a tip of the vapor delivery needle generally transverse to the shaft, wherein the deployment mechanism cannot move the vapor delivery needle more than 15 mm from the shaft;
   a scope bore in the shaft sized to accommodate an endoscope, the bore having an opening oriented to permit a user to view a distal end of the vapor delivery needle through the endoscope;
   a vapor source; and
   a vapor delivery actuator adapted to deliver vapor from the vapor source into the vapor delivery needle and out of the vapor exit port.

20. The system of claim 19 wherein the needle is movable between a retracted position in which a distal needle tip is within the shaft and a deployed position in which the distal needle tip extends from the shaft.

* * * * *